(12) United States Patent
Goodrich

(10) Patent No.: US 9,789,231 B2
(45) Date of Patent: Oct. 17, 2017

(54) RADIOPAQUE POLYMERS FOR MEDICAL DEVICES

(71) Applicant: ENDOSHAPE, INC., Boulder, CO (US)

(72) Inventor: Stephen D. Goodrich, Longmont, CO (US)

(73) Assignee: ENDOSHAPE, INC., Boulder, CO (US)

( * ) Notice: Subject to any disclaimer, the term of this patent is extended or adjusted under 35 U.S.C. 154(b) by 0 days.

(21) Appl. No.: 14/766,626

(22) PCT Filed: Feb. 7, 2014

(86) PCT No.: PCT/US2014/015250
§ 371 (c)(1),
(2) Date: Aug. 7, 2015

(87) PCT Pub. No.: WO2014/124225
PCT Pub. Date: Aug. 14, 2014

(65) Prior Publication Data
US 2015/0374884 A1    Dec. 31, 2015

Related U.S. Application Data

(60) Provisional application No. 61/762,416, filed on Feb. 8, 2013.

(51) Int. Cl.
*C08F 220/30* (2006.01)
*A61K 31/04* (2006.01)
(Continued)

(52) U.S. Cl.
CPC ........ *A61L 31/048* (2013.01); *A61K 49/0442* (2013.01); *A61L 31/18* (2013.01); (Continued)

(58) Field of Classification Search
CPC ..... A61L 31/048; A61L 3/18; A61K 2400/16; A61K 49/0442; C08F 222/18; C08F 8/20; C08F 220/30; C08F 220/22
See application file for complete search history.

(56) References Cited

U.S. PATENT DOCUMENTS 3,361,700 A   1/1968   Archer et al.
4,644,025 A   2/1987   Sakagami et al.
(Continued)

FOREIGN PATENT DOCUMENTS

EP   0685454   12/1995
EP   0710475    5/1996
(Continued)

OTHER PUBLICATIONS

Aldenhoff et al. (2002) "Stability of radiopaque iodine-containing biomaterials," Biomaterials. 23(3):881-886.
(Continued)

*Primary Examiner* — Sanza McClendon
(74) *Attorney, Agent, or Firm* — Lathrop Gage LLP

(57) ABSTRACT

Radiopaque polymer compositions and methods for making the compositions are provided. These radiopaque polymer compositions include polymer compositions comprising a crosslinked polymer network, the network comprising a first repeating unit derived from a monofunctional monomer and a second repeating unit derived from a multifunctional non-iodinated monomer wherein neither of the two monomers is fluorinated. Devices formed from radiopaque polymer compositions are also provided.

20 Claims, 3 Drawing Sheets a) Initial Entry b) Deployed

(51) Int. Cl.
*C08F 8/20* (2006.01)
*A61L 31/04* (2006.01)
*A61K 49/04* (2006.01)
*A61L 31/18* (2006.01)
*C08F 222/18* (2006.01)
*C08F 220/22* (2006.01)

(52) U.S. Cl.
CPC .............. *C08F 8/20* (2013.01); *C08F 220/30* (2013.01); *C08F 222/18* (2013.01); *A61L 2400/16* (2013.01); *C08F 220/22* (2013.01)

(56) References Cited

U.S. PATENT DOCUMENTS

| | | |
|---|---|---|
| 5,163,952 A | 11/1992 | Froix |
| 5,258,020 A | 11/1993 | Froix |
| 5,271,923 A | 12/1993 | Kochi et al. |
| 5,525,327 A | 6/1996 | Baker et al. |
| 5,599,291 A | 2/1997 | Balbierz |
| 5,674,241 A | 10/1997 | Bley |
| 5,674,242 A | 10/1997 | Phan |
| 5,679,710 A | 10/1997 | Davy et al. |
| 5,780,668 A | 7/1998 | Rheinberger et al. |
| 5,964,744 A | 10/1999 | Balbierz |
| 6,040,408 A | 3/2000 | Koole |
| 6,068,969 A | 5/2000 | Mikoshiba et al. |
| 6,160,084 A | 12/2000 | Langer et al. |
| 6,248,129 B1 | 6/2001 | Froix |
| 6,388,043 B1 | 5/2002 | Langer et al. |
| 6,475,477 B1 | 11/2002 | Kohn et al. |
| 6,509,406 B1 | 1/2003 | Brenner et al. |
| 6,550,480 B2 | 4/2003 | Feldman |
| 6,720,402 B2 | 4/2004 | Langer et al. |
| 6,887,266 B2 | 5/2005 | Williams |
| 7,115,691 B2 | 10/2006 | Alvarado |
| 7,208,550 B2 | 4/2007 | Mather |
| 7,217,744 B2 | 5/2007 | Lendlein et al. |
| 7,250,154 B2 | 7/2007 | Kohn et al. |
| 7,473,417 B2 | 1/2009 | Zeltinger et al. |
| 7,553,325 B2 | 6/2009 | Stinson |
| 9,062,141 B2 | 6/2015 | Goodrich et al. |
| 2004/0030062 A1 | 2/2004 | Mather |
| 2005/0033163 A1 | 2/2005 | Duchon et al. |
| 2005/0106119 A1 | 5/2005 | Brandom et al. |
| 2006/0024266 A1 | 2/2006 | Brandom et al. |
| 2006/0034769 A1 | 2/2006 | Kohn et al. |
| 2006/0036045 A1 | 2/2006 | Wilson |
| 2006/0036316 A1 | 2/2006 | Zeltinger et al. |
| 2006/0041089 A1 | 2/2006 | Mather |
| 2006/0095134 A1 | 5/2006 | Trieu et al. |
| 2006/0142794 A1 | 6/2006 | Lendlein et al. |
| 2006/0182779 A1 | 8/2006 | Brandom et al. |
| 2006/0213522 A1 | 9/2006 | Menchaca et al. |
| 2008/0009939 A1 | 1/2008 | Guerigian et al. |
| 2008/0228186 A1 | 9/2008 | Gall et al. |
| 2008/0281405 A1 | 11/2008 | Williams et al. |
| 2009/0023827 A1 | 1/2009 | Lendlein et al. |
| 2009/0248141 A1 | 10/2009 | Shandas et al. |
| 2011/0144227 A1 | 6/2011 | Bowman et al. |
| 2013/0225778 A1 | 8/2013 | Goodrich et al. |
| 2015/0374884 A1 | 12/2015 | Goodrich |
| 2016/0024239 A1 | 1/2016 | Goodrich et al. |

FOREIGN PATENT DOCUMENTS

| | | |
|---|---|---|
| GB | 1526888 | 10/1978 |
| GB | 2085012 | 4/1982 |
| JP | S60203607 | 10/1985 |
| JP | H08053515 | 2/1996 |
| JP | H08325203 | 12/1996 |
| JP | 2008239833 | 10/2008 |
| JP | 2004521172 | 7/2014 |
| WO | WO02/059170 | 8/2002 |
| WO | WO2005/109041 | 11/2005 |
| WO | WO2006/020616 | 2/2006 |
| WO | WO2007/084444 | 7/2007 |
| WO | WO2007/114823 | 10/2007 |
| WO | WO2007/115208 | 10/2007 |
| WO | WO2007/143698 | 12/2007 |
| WO | WO2008/033198 | 3/2008 |
| WO | WO2008/051279 | 5/2008 |
| WO | WO2008/054205 | 5/2008 |
| WO | WO2008/137235 | 11/2008 |
| WO | WO2008/138974 | 11/2008 |
| WO | WO2012/019145 | 2/2012 |
| WO | WO 2012019145 A1 * | 2/2012 ......... A61K 49/0442 |

OTHER PUBLICATIONS

Benzina et al. (Nov. 1994) "Studies on a new radiopaque polymeric biomaterial," Biomaterials. 15(14):1122-8.

Benzina et al. (Nov. 1996) "A versatile three-iodine molecular building block leading to new radiopaque polymeric biomaterials," J. Biomed. Mater. Res. 32(3):459-66.

Brown et al. (1985), "Syntheses and copolymerization of new water-soluble polyiodinated acrylic monomer", Makromol. Chem., Rapid Commun., 6(7), pp. 503-507.

Constant et al. (Sep. 2008) "Preparation, characterization, and evaluation of radiopaque hydrogel filaments for endovascular embolization," J. Biomed. Mater. Res. Part B: Appl. Biomater. 89B(2):306-313.

Cui et al. (Apr. 17, 2009) "Shape-Memory Properties of Radiopaque Micro-Composites from Amorphous Polyether Urethanes Designed for Medical Application," MRS Spring Meeting Materials Research Society.

Davy et al. (1996) "Novel iodinated methacrylates as X-ray opaque denture base polymers," J. Materials Science Letters. 35:656-657.

Davy et al. (1997) "X-Ray Opaque Methacrylate Polymers for Biomedical Applications," Polymer International. 43:143-154.

De Nardo et al. (Dec. 2008) "Shape memory polymer foams for cerebral aneurysm reparation: Effects of plasma sterilization on physical properties and cytocompatibility," Acta Biomaterialia. 5:1508-1518.

Extended European Search Report and Opinion corresponding to European Patent Application No. 14748815.9, dated Jan. 16, 2017.

Galperin et al. (2006) "Synthesis and characterization of new radiopaque microspheres by the dispersion polymerization of an iodinated acrylate monomer for X-ray imaging applications," J. Polymer Sci. Part A: Polymer Chem. 44(12):3959-3868.

Galperin et al. (2007) "Radiopaque iodinated polymeric nanoparticles for X-ray imaging applications," Biomaterials. 28(30):4461-4468.

Hampikian et al. (2006) "Mechanical and radiographic properties of a shape memory polymer composite for intracranial aneurysm coils," Mater. Sci. Engr. C. 26:1373-1379.

Heaton (Jul. 2004) "A Shape Memory Polymer for Intracranial Aneurysm Coils: An Investigation of Mechanical and Radiographic Properties of a Tantalum-Filled Shape Memory Polymer Composite," Thesis, Georgia Institute of Technology.

International Preliminary Report of Patentability corresponding to International Patent Application No. PCT/US14/15250, dated Aug. 11, 2015.

International Preliminary Report on Patentability corresponding to International Patent Application No. PCT/US14/28786, dated Sep. 15, 2015.

International Preliminary Report on Patentability corresponding to International Patent Application No. PCT/US11/46829, dated Feb. 12, 2013.

International Search Report and Written Opinion corresponding to International Patent Application No. PCT/US14/15250, dated May 9, 2014.

International Search Report and Written Opinion corresponding to International Patent Application No. PCT/US14/28786, dated Nov. 20, 2014.

International Search Report and Written Opinion corresponding to International Patent Application No. PCT/US11/46829, dated Dec. 9, 2011.

(56) References Cited

OTHER PUBLICATIONS

Jeon et al. (Jul. 2000) "Shape memory and nanostructure in poly(norbornyi-POSS) copolymers," Polymers International. 49:453-457.

Jeong et al. (2000) "Shape memory polyurethane containing amorphous reversible phase," J. Mat. Sci. 35:1579-1583.

Lendlein (2002) "Biodegradable, elastic shape-memory polymers for potential biomedical applications," Science. 296:1673-1676.

Lendlein et al. (2001) "AB-polymer networks based on oligo(epsilon-caprolactone) segments showing shape-memory properties," Proc. Nat. Acad. Sci. 98:3.842-847.

Lendlein et al. (2002) "Shape Memory Polymer," Advanced Chemie, International Edition. 41:2034-2057.

Li et al. (1999) "Shape memory effect of ethylene-vinyl acetate copolymers," J. App. Poly. Sci. 71:1063-1070.

Li et al. (2002) "New Soybean Oil-Styrene-Divinylbenzene Thermosetting Copolymers. V. Shape memory effect," J. App. Pol. Sci. 84:1533-1543.

Lin et al. (1998) "Study on Shape-Memory Behavior of Polyether-Based Polyurethanes. I. Influence of the Hard-Segment Content," J. App. Pol. Sci. 69:1563-1574.

Lin et al. (Aug. 22, 1998) "Study on Shape-Memory Behavior of Polyether-Based Polyurethanes. II. Influence of soft-segment molecular weight," Journal of Applied Polymer Science. 69(8):1575-1586.

Liu et al. (2002) "Chemically cross-linked polycyclooctene: Synthesis, characterization, and shape memory behavior," Macromolecules. 35:27.9868-9874.

Liu et al. (2003) "Thermomechanical Recovery Couplings of Shape Memory Polymers in Flexure," Smart Materials & Structures. 12:947-954.

Maitland (May 2007) "Prototype laser-activated shape memory polymer foam device for embolic treatment of aneurysms," J. Biomedical Optics (Letters). 12(3).030504-1-030504-3.

Moszner et al. (1995) "Synthesis and polymerization of hydrophobic iodine-containing methacrylates," Die Angewandte Makromolekulare Chemie. 224:115-123.

Sillion (2002) "Shape memory polymers," Act. Chimique. 3:182-188.

Small et al. (Mar. 2010) "Biomedical applications of thermally activated shape memory polymers," Journal of Materials Chemistry. 20:3356-3366.

Supplementary European Search Report corresponding to European Patent Application No. 14748815.9, dated Oct. 10, 2016.

Takahashi et al. (1996) "Structure and properties of shape memory polyurethane block copolymers," J. App. Pol. Sci. 60:1061-1069.

Van Hooy-Corstjens et al. (2004) "Mechanical behavior of a new acrylic radiopaque iodine-containing bone cement," Biomater. 25:2657-2667.

Wilson et al. (2005) "Shape Memory Polymer Therapeutic Devices for Stroke," Proc. of SPIE. 6007-60070R:60070R-1-60070R-8.

Yakacki et al. (2008) "Cytotoxicity and Thermomechanical behavior of biomedical shape memory polymer networks post sterilization," Biomedical Materials. 3:015010.9.

Yudina et al.(1989), Aspects of Direct Iodination of Polystyrene in Presence of [bis(Trifluoroacetoxy)Iodo]Benzene, *Polymer Science USSR*, 31(6), 1318-1823.

Zaharia (2008) "Chemical structure of methylmethacrylate-2[2',3',5'-triiodobenzoyl] oxoethyl methacrylate copolymer, radio-opacity, in vitro and in vivo biocompatibility," Acta Biomaterialia. 4:1762-1769.

Zhu et al. (2003) "Shape-memory effects of radiation crosslinked poly(epsilon-caprolactone)," J. App. Poly. Sci. 90:1589-1595.

First Office Action dated Mar. 22, 2017, corresponding to Chinese Patent Application No. 2014800197342.

\* cited by examiner a) Initial Entry b) Deployed

RADIOPAQUE POLYMERS FOR MEDICAL DEVICES

CROSS-REFERENCE TO RELATED APPLICATIONS

This application is a U.S. National Stage Application under 35 U.S.C. §371 of International Application No. PCT/US2014/015250, filed Feb. 7, 2014, which claims the benefit of U.S. Provisional Application No. 61/762,416, filed Feb. 8, 2013, each of which is hereby incorporated by reference in its entirety.

BACKGROUND

Shape memory materials are defined by their capacity to recover a predetermined shape after significant mechanical deformation (K. Otsuka and C. M. Wayman, "Shape Memory Materials" New York: Cambridge University Press, 1998). The shape memory effect is typically initiated by a change in temperature and has been observed in metals, ceramics, and polymers. From a macroscopic point of view, the shape memory effect in polymers differs from ceramics and metals due to the lower stresses and larger recoverable strains achieved in polymers.

The basic thermomechanical response of shape memory polymer (SMP) materials is defined by four critical temperatures. The glass transition temperature, $T_g$, is typically represented by a transition in modulus-temperature space and can be used as a reference point to normalize temperature for some SMP systems. SMPs offer the ability to vary $T_g$ over a temperature range of several hundred degrees by control of chemistry or structure. The predeformation temperature, $T_d$, is the temperature at which the polymer is deformed into its temporary shape. Depending on the required stress and strain level, the initial deformation $T_d$ can occur above or below $T_g$ (Y. Liu, K. Gall, M. L. Dunn, and P. McCluskey, "Thermomechanical Recovery Couplings of Shape Memory Polymers in Flexure." Smart Materials & Structures, vol. 12, pp. 947-954, 2003). The storage temperature, $T_s$, represents the temperature in which no shape recovery occurs and is equal to or is below $T_d$. The storage temperature $T_s$ is less than the glass transition temperature $T_g$. At the recovery temperature, $T_r$, the shape memory effect is activated, which causes the material to substantially recover its original shape. $T_r$ is above $T_s$ and is typically in the vicinity of $T_g$. Recovery can be accomplished isothermally by heating the material to a fixed $T_r$ and then holding, or by continued heating up to and past $T_r$. From a macroscopic viewpoint, a polymer will demonstrate a useful shape memory effect if it possesses a distinct and significant glass transition (B. Sillion, "Shape memory polymers," Act. Chimique., vol. 3, pp. 182-188, 2002), a modulus-temperature plateau in the rubbery state (C. D. Liu, S. B. Chun, P. T. Mather, L. Zheng, E. H. Haley, and E. B. Coughlin, "Chemically cross-linked polycyclooctene: Synthesis, characterization, and shape memory behavior." Macromolecules. vol. 35, no. 27, pp. 9868-9874, 2002), and a large difference between the maximum achievable strain, $\epsilon_{max}$, during deformation and permanent plastic strain after recovery, $\epsilon_p$ (F. Li, R. C. Larock, "New Soybean Oil-Styrene-Divinylbenzene Thermosetting Copolymers. V. Shape memory effect." J. App. Pol. Sci., vol. 84, pp. 1533-1543, 2002). The difference $\epsilon_{max}-\epsilon_p$ is defined as the recoverable strain, $\epsilon_{recover}$, while the recovery ratio is defined as $\epsilon_{recover}/\epsilon_{max}$.

The microscopic mechanism responsible for shape memory in polymers depends on both chemistry and structure (T. Takahashi, N. Hayashi, and S. Hayashi, "Structure and properties of shape memory polyurethane block copolymers." J. App. Pol. Sci., vol. 60, pp. 1061-1069, 1996; J. R. Lin and L. W. Chen, "Study on Shape-Memory Behavior of Polyether-Based Polyurethanes. II. Influence of the Hard-Segment Content." J. App. Pol. Sci., vol. 69, pp. 1563-1574, 1998; J. R. Lin and L. W. Chen, "Study on Shape-Memory Behavior of Polyether-Based Polyurethanes. I. Influence of soft-segment molecular weight." J. App. Pol. Sci., vol 69, pp. 1575-1586, 1998; F. Li, W. Zhu, X. Zhang, C. Zhao, and M. Xu, "Shape memory effect of ethylene-vinyl acetate copolymers." J. App. Poly. Sci., vol. 71, pp. 1063-1070, 1999; H. G. Jeon, P. T. Mather, and T. S. Haddad, "Shape memory and nanostructure in poly(norbornyl-POSS) copolymers." Polym. Int., vol. 49, pp. 453-457, 2000; H. M. Jeong, S. Y. Lee, and B. K. Kim, "Shape memory polyurethane containing amorphous reversible phase." J. Mat. Sci., vol. 35, pp. 1579-1583, 2000; A. Lendlein, A. M. Schmidt, and R. Langer, "AB-polymer networks based on oligo (epsilon-caprolactone) segments showing shape-memory properties." Proc. Nat. Acad. Sci., vol. 98, no. 3, pp. 842-847, 2001; G. Zhu, G. Liang, Q. Xu, and Q. Yu, "Shape-memory effects of radiation crosslinked poly(epsilon-caprolactone)." J. App. Poly. Sci., vol. 90, pp. 1589-1595, 2003). One driving force for shape recovery in polymers is the low conformational entropy state created and subsequently frozen during the thermomechanical cycle (C. D. Liu, S. B. Chun, P. T. Mather, L. Zheng, E. H. Haley, and E. B. Coughlin, "Chemically cross-linked polycyclooctene: Synthesis, characterization, and shape memory behavior." Macromolecules. Vol. 35, no. 27, pp. 9868-9874, 2002). If the polymer is deformed into its temporary shape at a temperature below $T_g$, or at a temperature where some of the hard polymer regions are below $T_g$, then internal energy restoring forces will also contribute to shape recovery. In either case, to achieve shape memory properties, the polymer must have some degree of chemical crosslinking to form a "memorable" network or must contain a finite fraction of hard regions serving as physical crosslinks.

SMPs are processed in a manner that is termed programming, whereby the polymer is deformed and set into a temporary shape. (A. Lendlein, S. Kelch, "Shape Memory Polymer," Advanced Chemie, International Edition, 41, pp. 1973-2208, 2002.) When exposed to an appropriate stimulus, the SMP substantially reverts back to its permanent shape from the temporary shape. The stimulus may be, for example, temperature, magnetic field, water, or light, depending on the initial monomer systems.

For SMPs used in medical devices, wherein temperature is the chosen stimulus, an external heat source may be used to provide discretionary control of the shape recovery by the physician, or the body's core temperature may be utilized to stimulate the shape recovery upon entry or placement within the body from the environmental temperature, which may be room temperature. (Small W, et al "Biomedical applications of thermally activated shape memory polymers" Journal of Materials Chemistry, Vol 20, pp 3356-3366, 2010.)

For implantable medical devices, the life expectancy of the device can be defined by the duration that it must maintain its mechanical properties and functionality in the body. For biodegradable devices, this life expectancy is intentionally short, providing a mechanism for the material and device to degrade over time and be absorbed by the body's metabolic processes. For non-biodegradable devices, referred to as biodurable devices, or devices exhibiting biodurability, they are not intended to degrade and they must maintain their material properties and functionality for longer periods, possibly for the life the patient.

For medical devices used within the body, either permanent implants or instrumentation used for diagnostic or therapeutic purposes, the ability to visualize the device using typical clinical imaging modalities, e.g. X-ray, Fluoroscopy, CT Scan, and MRI is typically a requirement for clinical use. Devices intended to be imaged by X-ray and Fluoroscopy, typically contain either metals or metal byproducts to induce radiopacity. Radiopacity refers to the relative inability of electromagnetism, particularly X-rays, to pass through dense materials, which are described as 'radiopaque' appearing opaque/white in a radiographic image. A more radiopaque material appears brighter, whiter, on the image. (Novelline, Robert. Squire's Fundamentals of Radiology. Harvard University Press. 5th edition. 1997.) Given the complexity of the content within an X-ray or Fluoroscopic image, clinicians are sensitive to the quality of the image regarding the brightness or signal strength of the material in the image. The two main factors that contribute to radiopacity brightness, or signal strength of a material are density and atomic number. Polymer based medical devices requiring radiopacity typically utilize a polymer blend that incorporates a small amount, by weight percent, of a heavy atom, radiopaque filler such as Titanium Dioxide ($TiO_2$), or Barium Sulfate ($BaSO_4$). The device's ability to be visualized on fluoroscopy is dependent upon the amount, or density, of the filler mixed into the material, which is typically limited to a small quantity as the filler can detrimentally affect the base polymer's material properties. Meanwhile, medical device imaging companies have developed standardized liquid contrast media to be intermittently used by physicians to highlight vascular structures, etc. during X-ray or Fluoroscopy when filled with this contrast media. This media commonly contains a heavy atom fluid, such as iodine, to induce radiopacity.

Iodine-incorporating monomers were reported by Mosner et al., who reported 3 different triiodinated aromatic monomers, which differed in the degree to which they could be homopolymerized or required copolymerization in order to be incorporated. (Moszner et al "Synthesis and polymerization of hydrophobic iodine-containing methacrylates" Die Angewandte Makromolekulare Chemie 224 (1995) 115-123) Iodinating monomers were also pursued by Koole et al in the Netherlands, as published from 1994-1996 with a range of monoiodinated to triiodinated aromatic monomers (Koole et al "Studies on a new radiopaque polymeric biomaterial," Biomaterials 1994 November; 15(14):1122-8. Koole et al "A versatile three-iodine molecular building block leading to new radiopaque polymeric biomaterials," J Biomed Mater Res, 1996 November; 32(3):459-66). This included biocompatibility results of a 2-year implantation study in rats of monoiodinated aromatic methacrylate copolymer systems. (Koole et al "Stability of radiopaque iodine-containing biomaterials," Biomaterials 2002 February; 23(3):881-6) They are also discussed by Koole in U.S. Pat. No. 6,040,408, filed initially as a European patent application in August, 1994, which limits its claims to aromatic monomers containing no more than two covalently bonded iodine groups. (U.S. Pat. No. 6,040,408, "Radiopaque Polymers and Methods for Preparation Thereof," Koole, 21 Mar. 2000). Also, US Patent Application 20060024266 by Brandom et al. claimed polyiodinated aromatic monomers in shape memory polymers, emphasizing the use of crystallizable polymer side-groups (US Patent Application 20060024266, "Side-chain crystallizable polymers for medical applications, Brandom et al, 5 Jul. 2005).

The information included in this Background section of the specification, including any references cited herein and any description or discussion thereof, is included for technical reference purposes only and is not to be regarded subject matter by which the scope of the invention is to be bound.

BRIEF SUMMARY

In one aspect, the invention provides radiopaque polymers. In one aspect, the radiopaque polymers are shape memory polymers (SMPs). In one aspect, the compositions and compounds disclosed are useful for medical devices. In one aspect, the compositions and compounds disclosed may be shape memory polymers as defined herein and known in the art, but are not used in a manner in which they are externally triggered. In one aspect, the compositions and compounds disclosed are "space-triggered", as the phrase is conventionally used. In a space triggered material the materials return to their original shape upon removal of a spatial constraint, as is the case when a coil-shaped specimen emerges from its temporary elongated configuration within a deployment catheter and regains its coil shape, for example. It should be made clear that certain compositions and compounds described herein may technically have shape memory properties, but those properties may or may not be used in the devices and methods of the invention. As used herein, the compounds and compositions described and disclosed here are intended to include shape memory aspects and non-shape memory aspects as applicable. If a particular embodiment is described using a shape memory polymer, it is recognized that other compounds and compositions that are not specifically defined as having shape memory properties may be interchangeable and used in that embodiment.

In an embodiment, the polymers of the invention do not contain any metal materials or metal components or elements but still exhibit suitable radiopacity for clinical viewing using conventional imaging systems. Clinicians are commonly challenged by obscuring artifacts from metal and metal based implanted devices when attempting to image using either CT scan (Computed Tomography) or MRI (Magnetic Resonance Imaging). The significance of the artifact is typically based upon the amount of metal content and can be so excessive as to inhibit the ability to clinically image the device. This situation can require an alternative means to clinically evaluate the patient or device (e.g. angiogram, etc.) which may not only be more costly, but more invasive and risky to the patient. As such, a non-metallic, radiopaque polymer reflects a significant advantage and differentiation from other approaches for radiopaque devices. In an embodiment, a device disclosed contains metal. In one aspect, a device disclosed contains metal in the form of marker bands, as conventionally used for visualization. In one aspect, the devices disclosed comprise platinum-iridium or gold marker bands, as known in the art. As known in the art, "marker bands" may be used to achieve a specific product requirement, such as demarcation of an edge of the device or alignment of two devices for proper use, for example. The use of marker bands is optional with the devices described herein.

The compositions and compounds disclosed comprise a radiopaque functionality. In an aspect, the radiopaque functionality is one or more iodine atoms. In an aspect, the radiopaque functionality is one or more Br or Bi atoms. In an embodiment, the compositions and compounds of the invention include covalently bound heavy atoms such as iodine. In this embodiment, the distribution of iodine or other radiopaque functionality within the polymer is sufficiently homogeneous so as to be efficacious for imaging applications.

In an embodiment, the polymers of the present invention are sufficiently amorphous that some conventional analysis methods do not indicate the presence of residual amounts of crystallinity. In an embodiment, the polymers described herein are not sufficiently crystalline as to cause devices incorporating the polymers to be inoperative in the desired uses. In general, if shape memory polymers are semicrystalline, shape change can be hindered and slowed, and device performance can become clinically undesirable. The crystallinity of the shape memory polymer and non-shape memory polymers described here can be affected by the selection of the components used to form the polymer, as further described herein.

In an embodiment, the glass transition temperature and rubbery modulus of the polymers of the present invention can be adjusted independently, as further described herein.

In an embodiment, the invention provides a polymer which has sufficient resistance to water absorption that it can be used to fabricate medical devices or device components for use in a physiological environment with exposure to body fluid(s). In an embodiment, the medical devices or device components show little change in their mechanical properties or degradation of their mechanical integrity during the useful lifetime of the device. In an embodiment, the devices and compositions described here are useful for permanent (or long-term) implantation or use in a biological system. In an embodiment, devices or device components formed using the polymer compositions of the invention exhibit a water uptake of less than 1.0% by weight over a 24 hour period. In an embodiment, devices or device components formed using the polymer compositions of the invention exhibit a water uptake of less than 0.5% by weight over a 24 hour period.

In one embodiment, the invention provides a polymer composition comprising a crosslinked polymer network, the network comprising a first repeating unit derived from a monofunctional radiopaque monomer and a second repeating unit derived from a multifunctional non-radiopaque monomer wherein neither the first nor the second monomer is fluorinated. The first repeating unit may be derived from the monomer of any of Formulas 8, 8-A, 8-B, 8-C, 13, 13-A, 14, 15, 16, 17 or 18. In an embodiment, the second monomer is a multifunctional "hydrophobic" crosslinking monomer that imparts enhanced biodurability properties. In an embodiment, the crosslinking monomer is other than poly(ethylene glycol) di(meth)acrylate (PEGDA or PEGDMA). The multifunctional crosslinker molecule may have two or more polymerizable functional groups, such as acrylate groups. The second repeating unit may be derived from the monomer of any of formulas 9, 9-A, 9-B, 9-C, or 19. In different embodiments, the polymer composition may include repeating units derived from one or more monofunctional iodinated and/or non-iodinated co-monomers and/or one or more multifunctional crosslinking monomers. In an embodiment, the amount of the first repeating unit derived from the radiopaque monomer may be from 15 wt % to 35 wt % or 20-30 wt % of the polymer composition, while the amount of the repeating unit(s) derived from the crosslinking monomer(s) may be from 85 wt % to 65 wt % or 80-70 wt % of the monomer mixture. In an embodiment, the relative amount of the repeating units in the network derived from each type of monomer is the same as the relative amount of the respective monomers in the monomer mixture.

In an embodiment, the crosslinked network is characterized by covalent bonding between said first repeating unit and said second repeating unit such that the second repeating unit forms the crosslinking of the crosslinked network.

In an embodiment, the iodinated monomer contains an average of between 1 to 4, 2 to 4 or 3 to 4 iodine atoms per repeating unit. In an embodiment, the first repeating unit is an acrylate ester of 2,3,5-triiodobenzoic acid. In an embodiment, the second monomer is a multifunctional "hydrophobic" crosslinking monomer. In an embodiment, the crosslinking monomer is other than poly(ethylene glycol) di(meth)acrylate (PEGDA or PEGDMA). The multifunctional crosslinker molecule may have two or more polymerizable functional groups, such as acrylate groups. In different embodiments, the polymer composition may include repeating units derived from one or more monofunctional iodinated and/or non-iodinated co-monomers and/or one or more multifunctional crosslinking monomers. In different embodiments, there is more than one crosslinking monomer used in the compounds and compositions provided. In an embodiment, a crosslinking monomer is polycarbonate diacrylate. In an embodiment, a crosslinking monomer is decanediol-diacrylate. In an embodiment, a crosslinking monomer has a polymer backbone that causes the structure to have the characteristics of an elastomer, a reinforced plastic, or any other polymer backbone capable of producing a desirable functional outcome for the final crosslinked product. In an embodiment, a crosslinking monomer is multifunctional.

Use of monomers with different chemical structures and amounts thereof can be used to suppress formation of crystalline regions in the polymer. In an embodiment, the monomers are selected for phase compatibility in the liquid and solid state. Phase compatibility of the monomers can facilitate random incorporation of the monomer units during free radical polymerization and homogeneity in the resulting polymer.

In an embodiment, a first repeating unit is an iodinated monofunctional acrylate monomer comprising an iodinated $C_5$-$C_{36}$ aryl or $C_5$-$C_{36}$ heteroaryl. In an embodiment, the repeating unit derived from the iodinated monomer has the general formula:

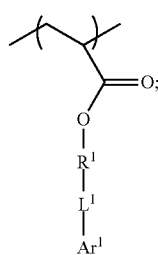

(Formula 1)

wherein $R^1$ is substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, or $C_5$-$C_{36}$ heteroarylene; $L^1$ is a single bond, —$(CH_2)_n$—, —$(HCCH)_n$—, —O—, —S—, —SO—, —$SO_2$—, —$SO_3$—, —$OSO_2$—, —$NR^2$—, —CO—, —COO—, —OCO—, —OCOO—, —$CONR^3$—, —$NR^4CO$—, —$OCONR^5$—, —$NR^6COO$—, or —$NR^7CONR^8$—; $Ar^1$ is a $C_5$-$C_{30}$ aryl or $C_5$-$C_{30}$ heteroaryl that is substituted with three or more I, Br or Bi atoms; and each of $R^2$-$R^8$ is independently hydrogen or $C_1$-$C_{10}$ alkyl; n is an integer selected from the range of 1 to 16. In an embodiment, $L^1$ is ester or amide.

In an embodiment, the formula of the first repeating unit may be given by

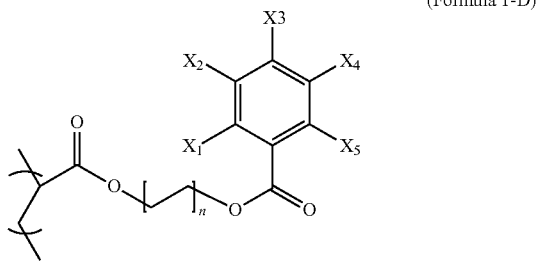

(Formula 1-D)

Formula 1-D wherein each of $X_1$-$X_5$ are either a radiopaque moiety or hydrogen and n is from 1 to 8. In an embodiment, the integer n is from 1 to 3 and at least two of $X_1$-$X_5$ may be iodine or at least three of $X_1$-$X_5$ may be iodine.

In an embodiment, a second repeating unit is a non-iodinated multifunctional crosslinker monomer unit. In an embodiment, the second repeating unit is a diacrylate crosslinker monomer unit. In an embodiment, the repeating unit derived from the crosslinker monomer has the general formula:

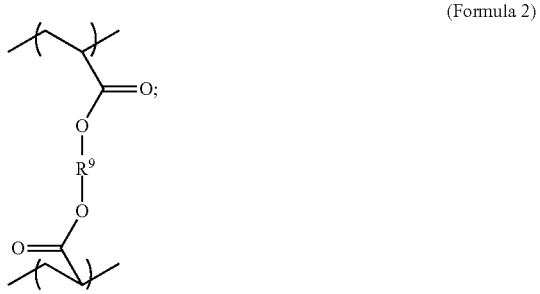

(Formula 2)

wherein $R^9$ is substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, an oligomeric polyester, an oligomeric polycarbonate, an oligomeric polyurethane,

(Formula 3)

(Formula 4)

(Formula 4-A)

wherein $R^{10}$ is $C_4$-$C_{20}$ alkylene and $n_3$ is an integer from 1 to 50 or wherein $R^{11}$ is $C_3$-$C_{20}$ alkylene and $n_4$ is an integer from 1 to 50; where $R^{15}$ is aliphatic group, substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, aromatic group, polyalkyl siloxane group, polyether group, polyester group, polycarbonate group, or a combination of linear or branched aliphatic groups and aromatic groups and $R^{16}$ is ether group, polyalkyl siloxane group, polyether group, polyester group, polycarbonate group, $C_3$-$C_{20}$ alkylene, aliphatic group, substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, or aromatic group, or a combination of aliphatic groups and aromatic groups and $n_5$ is an integer from 1 to 50. In an embodiment, $R_{16}$ is not poly(ethylene glycol) PEG.

In an embodiment, Formula 4-A is according to the following Formula 4-B:

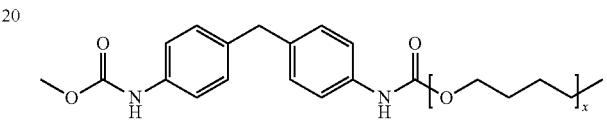

where x is an integer from 1 to 50.
(Formula 4-B)

As used herein, a monomer can include oligomer or polymer chains of different molecular mass, leading to a molecular weight distribution. When a monomer formula is given that includes an internal repeating group (e.g. —$R^{10}$—O— in Formula 3), the monomer can include chains with varying numbers of the internal repeating group (e.g. for Formula 3, a range can exist for $n_3$). Consequently, the repeating units derived from the monomer can also have a distribution of molecular mass (e.g. for the repeating unit according to Formula 2, when $R^9$ is given by Formula 3, a range can exist for $n_3$).

In an embodiment, a non-iodinated crosslinker monomer is an oligomeric polyester, an oligomeric polycarbonate, an oligomeric polyurethane, or another oligomeric homopolymer or copolymer. In an embodiment, the molecular weight of the oligomer is less than 1000. In an embodiment, the molecular weight of the oligomer is greater than or equal to 500 and less than 1000. In an embodiment, the molecular weight of the oligomer is any molecular weight that produces a composition having properties that are useful in the desired use. In an embodiment, the molecular weight of the oligomer is greater than 1000 and less than 10,000. The molecular weight of the oligomer may be greater than 1000 and less than 2500, greater than 1500 and less than 2500, or greater than 2000 and less than 2500. In an embodiment, the dispersity or polydispersity index may be from 1.0 to 10. In an embodiment, the oligomeric polyester crosslinker is a poly ($C_2$-$C_{36}$ carbonate) diacrylate. In another embodiment, the crosslinker monomer comprises a polycondensate of one or more compounds selected from the group consisting of: diacid chloride, diol, diisocyanate, and bis-chloroformate. In an embodiment, when the structure of the crosslinker molecule is according to Formula 9, the number of atoms in $R^9$ may be from 10 to 100. The compounds used to form the polycondensate can be linear or branched aliphatic, cycloaliphatic, partially cycloaliphatic or partially aromatic. In an embodiment, the compounds used to form the polycondensate may be linear or branched aliphatic or cycloaliphatic.

In an aspect, the formula of the second repeating unit may be given by Formula 2, with $R^9$ being $C_2$-$C_{36}$ alkylene, or by Formula 2-B where $R^{11}$ is $C_3$-$C_{20}$ alkylene and $n_4$ is an integer from 1 to 50, 1 to 25 or 1 to 10.

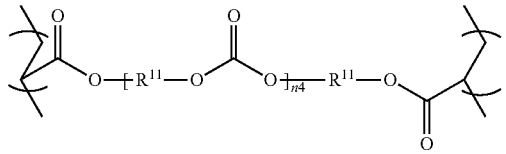

(Formula 2-B)

The polymer network may also comprise repeating units derived from at least two crosslinker monomers. The two crosslinker monomers may be any suitable structure shown or described here. The repeating units from the crosslinker monomers may all be derived from diacrylate crosslinker monomers. The repeating units for the second crosslinker molecule may be also be generally described by Formula 2, although the first and second crosslinker molecules are not identical. In addition, the repeating units for a second crosslinker monomer may be described by Formula 7. In an embodiment, the relative amounts of the repeating units derived from the first and the second crosslinking monomer can be equal. In another embodiment, the relative amount of the repeating units due to the first crosslinking monomer, relative to the total amount of the repeating units due to crosslinking monomers, may be 0 to 80 wt % or 50-70 wt %. If only two crosslinking monomers are present, the amount of repeating units due to the second monomer may be 20-60 wt % or 30%-50 wt % relative to the total amount of the repeating units derived from crosslinking monomers. The first crosslinking monomer may be of higher molecular weight than the second crosslinking monomer.

The polymer network may further comprise a repeating unit derived from a monofunctional non-iodinated monomer. In an embodiment, this repeating unit may be described by Formula 5 or any suitable structure shown or described here.

In another aspect, the invention also provides methods for making radiopaque polymers comprising a crosslinked network. In an embodiment, the method comprises the steps of:
a) forming a monomer mixture comprising
i) a first monomer having the general structure

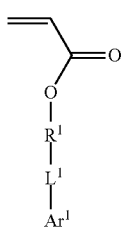

(Formula 8)

where $R^1$ is substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, or $C_5$-$C_{36}$ heteroarylene; $L^1$ is a single bond, —$(CH_2)_n$—, —$(HCCH)_n$—, —O—, —S—, —SO—, —$SO_2$—, —$SO_3$—, —$OSO_2$—, —$NR^2$—, —CO—, —COO—, —OCO—, —OCOO—, —$CONR^3$—, —$NR^4CO$—, —$OCONR^5$—, —$NR^6COO$—, or —$NR^7CONR^8$—; $Ar^1$ is a $C_5$-$C_{30}$ aryl or $C_5$-$C_{30}$ heteroaryl that is substituted with three or more I, Br or Bi atoms; and each of $R^2$-$R^8$ is independently hydrogen or $C_1$-$C_{10}$ alkyl; n is an integer selected from the range of 1 to 16 ii) a second monomer having the general structure of Formula 9

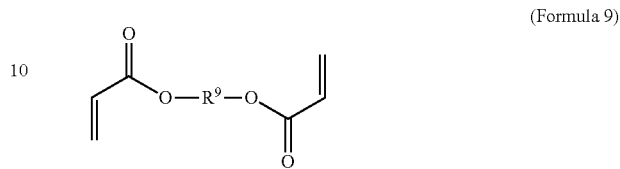

(Formula 9)

where $R^9$ is substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, an oligomeric polyester, an oligomeric polycarbonate, an oligomeric polyurethane,

(Formula 3)

(Formula 4)

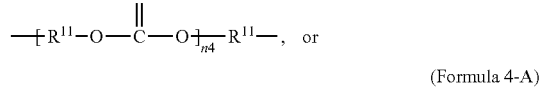

(Formula 4-A)

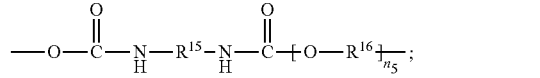

wherein $R^{10}$ is $C_4$-$C_{20}$ alkylene and $n_3$ is an integer from 1 to 50 or wherein $R^{11}$ is $C_3$-$C_{20}$ alkylene and $n_4$ is an integer from 1 to 50; where $R^{15}$ is aliphatic group, substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, aromatic group, polyalkyl siloxane group, polyether group, polyester group, polycarbonate group or a combination of linear or branched aliphatic groups and aromatic groups and $R^{16}$ is ether group, polyalkyl siloxane group, polyether group, polyester group, polycarbonate group, $C_3$-$C_{20}$ alkylene, aliphatic group, substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, or aromatic group, or a combination of aliphatic groups and aromatic groups and $n_5$ is an integer from 1 to 50; and
iii) a free radical initiator; and
b) polymerizing the monomer mixture.

The monomer mixture may further comprise a monofunctional non-iodinated monomer. This monofunctional non-iodinated monomer may be an acrylate monomer or other monomer or precursor described herein. In an embodiment, the monofunctional non-iodinated monomer may be as described by Formula 10, where $R_{12}$ may be from $C_2$ to $C_{36}$ alkyl, $C_2$-$C_{10}$ alkyl or $C_4$ alkyl. In different embodiments, the amount of comonomer may be from 2.5-90 wt %, 5-80 wt %, 10-80 wt %, 20-90 wt %, 2.5-10 wt %, 5-50 wt %, 5-25 wt %, 25-50 wt %, 50-80 wt %, 10-50 wt %, 20-50 wt %, or 10-70 wt % and all lower, intermediate, and higher values and ranges therein.

The monomer mixture may further comprise at least one additional multifunctional crosslinking monomer. In an embodiment, one of the crosslinking monomers may be of higher molecular weight than the other(s). In an embodiment, one of the crosslinking monomers may have a molecular weight greater than or equal to 200 and less than 500 while the other may have a molecular weight greater than or equal to 500 and less than or equal to 1000. In an embodiment, the weight percentage of the higher molecular weight crosslinking monomer is from 5-80 wt % of the monomer mixture while the weight percentage of the lower molecular weight crosslinking monomer is from 1-50 wt % of the monomer mixture. In an embodiment, the weight percentage of the higher molecular weight crosslinking monomer is from 10-55 wt % while the weight percentage of the lower molecular weight crosslinking monomer is from 1% to 35%. In an embodiment, the weight percentage of the higher molecular weight crosslinking monomer is from 20-50 wt % while the weight percentage of the lower molecular weight crosslinking monomer is from 1% to 35%. and all other permutations yielding a useful composition for the intended use.

In another aspect, the invention provides radiopaque medical devices. The original molded shape of radiopaque medical devices of the present invention can be deformed into a temporary shape typically having a reduced profile to facilitate insertion into a vessel, lumen, or other aperture or cavity. After insertion, the device can self-expand to assume a deployed configuration. In an embodiment, the medical device may assume its deployed configuration due to changes in temperature or other stimuli. In an embodiment, these SMP devices are capable of exhibiting shape memory behavior at physiological temperatures and may be used in surgical and catheter based procedures. In an embodiment, the medical device's deployed configuration may have one or more useful purposes including lumen occlusion, lumen opening or stenting, device anchoring or retention, patching or sealing a surface, structural restoration or localized drug delivery. The devices may use a SMP property of the compound or composition or may not use this property, if found in the compound or composition.

In another aspect, the invention also provides a radiopaque polymer device for medical applications, the device or device feature comprising a polymer composition according to the present invention. In an embodiment, the device's propensity for water uptake is less than 1.0% by weight over a 24 hour period.

In an embodiment, the glass transition temperature of the polymer may be from 25° C. to 50° C. In an embodiment, the glass transition temperature of the polymer is from 15° C. to 75° C., though any other polymer glass transition temperature that produces a useful final product is intended to be included as well. In some embodiments, the glass transition temperature may be suppressed below body temperature. When a polymer formed from such a device is delivered in a catheter or other delivery device, the material may already transition to its rubbery state in the delivery device. This can allow achievement of a more rapid response (elastic response) from the device after delivery (e.g. in the vessel). The polymer composition may be a shape memory polymer having a glass transition temperature (Tg) between 15° C. to 75° C. and a rubbery modulus between 0.1 MPa and 500 MPa at 37° C. The polymer may be such that Tg is at or below body temperature. the polymer exhibits a glass transition temperature (Tg) and a Tan Delta (Loss Modulus/Storage Modulus ratio) curve related to temperature; the polymer's maximum rate of shape change occurs at an environmental operating temperature (To) that is coincident with the temperature at which the material's Tan Delta value is ≤60% of its peak value, above Tg.

In the formulas provided herein, when linker $L_1$ is a single bond, then $R^1$ and $Ar^1$ are directly linked via a single bond. In an embodiment, the invention provides polymer compositions comprising a first repeating unit of formula 1, formula 1A, formula 1B or formula 1C, wherein $L^1$ is a single bond, thereby providing direct linking between $R^1$ and $Ar^1$ via a single bond.

As used herein, the term "group" may refer to a functional group of a chemical compound. Groups of the present compounds refer to an atom or a collection of atoms that are a part of the compound. Groups of the present invention may be attached to other atoms of the compound via one or more covalent bonds. Groups may also be characterized with respect to their valence state. The present invention includes groups characterized as monovalent, divalent, trivalent, etc. valence states.

As used throughout the present description, the expression "a group corresponding to" an indicated species expressly includes a moiety derived from the group including a monovalent, divalent or trivalent group.

As is customary and well known in the art, hydrogen atoms in the Formulas included are not always explicitly shown, for example, hydrogen atoms bonded to the carbon atoms of the polymer backbone, crosslinking groups, aromatic group, etc. The structures provided herein, for example in the context of the description of the Formulas, are intended to convey to one of reasonable skill in the art the chemical composition of compounds of the methods and compositions of the invention, and as will be understood by one of skill in the art, the structures provided do not indicate the specific positions of atoms and bond angles between atoms of these compounds.

As used herein, the terms "alkylene" and "alkylene group" are used synonymously and refer to a divalent group derived from an alkyl group as defined herein. The invention includes compounds having one or more alkylene groups. Alkylene groups in some compounds function as attaching and/or spacer groups. Compounds of the invention may have substituted and/or unsubstituted $C_1$-$C_{20}$ alkylene, $C_1$-$C_{10}$ alkylene and $C_1$-$C_5$ alkylene groups.

As used herein, the term "halo" refers to a halogen group such as a fluoro (—F), chloro (—Cl), bromo (—Br), iodo (—I) or astato (—At).

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. The term cycloalkyl specifically refers to an alky group having a ring structure such as ring structure comprising 3-30 carbon atoms, optionally 3-20 carbon atoms and optionally 2-10 carbon atoms, including an alkyl group having one or more rings. Cycloalkyl groups include those having a 3-, 4-, 5-, 6-, 7-, 8-, 9- or 10-member carbon ring(s) and particularly those having a 3-, 4-, 5-, 6-, or 7-member ring(s). The carbon rings in cycloalkyl groups can also carry alkyl groups. Cycloalkyl groups can include bicyclic and tricycloalkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group that has been modified by linkage to oxygen and can be represented by the formula R—O and can also be referred to as an alkyl ether group. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups. As used herein MeO— refers to $CH_3O$—.

Aryl groups include groups having one or more 5-, 6- or 7-member aromatic and/or heterocyclic aromatic rings. The term heteroaryl specifically refers to aryl groups having at least one 5-, 6- or 7-member heterocyclic aromatic rings. Aryl groups can contain one or more fused aromatic and heteroaromatic rings or a combination of one or more aromatic or heteroaromatic rings and one or more non-aromatic rings that may be fused or linked via covalent bonds. Heterocyclic aromatic rings can include one or more N, O, or S atoms in the ring. Heterocyclic aromatic rings can include those with one, two or three N atoms, those with one or two O atoms, and those with one or two S atoms, or combinations of one or two or three N, O or S atoms. Aryl groups are optionally substituted. Substituted aryl groups include among others those which are substituted with alkyl or alkenyl groups, which groups in turn can be optionally substituted. Specific aryl groups include phenyl, biphenyl groups, pyrrolidinyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic group, including monovalent, divalent and polyvalent groups, of the aromatic and heterocyclic aromatic groups listed herein are provided in a covalently bonded configuration in the compounds of the invention at any suitable point of attachment. In embodiments, aryl groups contain between 5 and 30 carbon atoms. In embodiments, aryl groups contain one aromatic or heteroaromatic six-membered ring and one or more additional five- or six-membered aromatic or heteroaromatic ring. In embodiments, aryl groups contain between five and eighteen carbon atoms in the rings. Aryl groups optionally have one or more aromatic rings or heterocyclic aromatic rings having one or more electron donating groups, electron withdrawing groups and/or targeting ligands provided as substituents.

DETAILED DESCRIPTION

Figure 1:
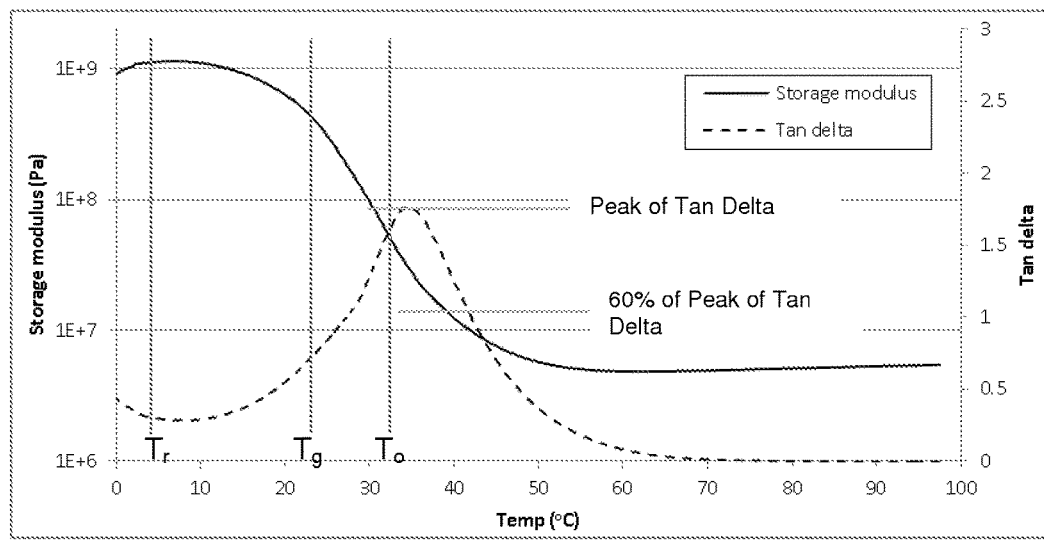
FIG. 1: DMA curve for an SMP formulation with examples of $T_r$, $T_g$, $T_o$ and Tan Delta Peak.

As used herein, a crosslinked network is a polymer composition comprising a plurality of polymer chains wherein a large portion (e.g., ≥80%) and optionally all the polymer chains are interconnected, for example via covalent crosslinking, to form a single polymer composition. In an embodiment, the invention provides a radiopaque polymer in the form of a crosslinked network in which at least some of the crosslinks of the network structure are formed by covalent bonds. Radiopacity refers to the relative inability of electromagnetism, particularly X-rays, to pass through dense materials. The two main factors contributing to a material's radiopacity are density and atomic number of the radiopaque element. In an embodiment, this invention utilizes incorporated (trapped) iodine molecules within the polymer matrix to induce radiopaque functionality. In an embodiment, the radiopaque polymer is an iodinated polymer. As referred to herein, iodinated polymers are produced by incorporating (trapping) iodine molecules on a select monomer prior to formulation of the monomer into a polymer. In different embodiments, the concentration of iodine in the radiopaque polymer is at least 200 or at least 300 mg/mm$^3$. Although iodine is used in some examples and descriptions herein, it is recognized that other radiopaque materials may be used, such as Bi and Br and that the descriptions here apply to and may be used with other radiopaque materials.

In an embodiment, the iodinated crosslinked polymers of the invention are formed by the polymerization of a monomer mixture comprising an iodinated monofunctional monomer, a multifunctional crosslinking monomer, and an initiator. The monomer mixture may also comprise one or more additional iodinated monofunctional monomers, one or more additional crosslinking monomers, and/or one or more additional monofunctional monomers. As used herein, "monofunctional" refers to a monomer containing only one polymerizable group, while "multifunctional" refers to a monomer containing more than one polymerizable group. Upon polymerization, the monomers in the monomer mixture contribute constitutional units to the network, with each constitutional unit being an atom or group of atoms (with pendant atoms or groups, if any) comprising a part of the essential structure of a macromolecule, an oligomer molecule, a block or a chain. Since the constitutional units typically appear multiple times in the network, they may also be termed repeating units. Repeating units derived from a given type of monomer need not be located adjacent to one another in the network or in a given sequence in the network. In an embodiment, the monofunctional iodinated monomer comprises an acrylate polymerizable group. In another embodiment, the monofunctional iodinated monomer comprises a styrene, acrylamide, or methacrylamide polymerizable group. In an embodiment, the polymerizable group is an end group. In an embodiment, the polymer compositions further comprise repeating units derived from a monofunctional iodinated monomer comprising a styrene, acrylamide or methacrylamide polymerizable group.

As used herein, an iodinated monomer comprises an iodine-containing moiety. In an embodiment, the iodinated monomer comprises an iodine-containing moiety which is an iodinated aryl or heteroaryl group. In an embodiment, the iodine-containing moiety is $C_5$-$C_{30}$ aryl or $C_5$-$C_{30}$ heteroaryl having at least 1 iodine atom. In an embodiment, the iodine-containing moiety is $C_5$-$C_{30}$ aryl or $C_5$-$C_{30}$ heteroaryl having at least 2 iodine atoms. In an embodiment, the iodine-containing moiety is $C_5$-$C_{30}$ aryl or $C_5$-$C_{30}$ heteroaryl having at least 3 iodine atoms. In an embodiment, the iodine-containing moiety is $C_6$ aryl with iodine atoms attached directly to the ring, with the number of iodine atoms being from 3 to 5. As is known in the art, the description herein can be used for embodiments using Br or Bi as radiopaque moieties.

In an embodiment, the iodinated monomer may be described by the general formula shown in Formula 8.

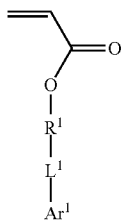

(Formula 8)

In an embodiment, $R^1$ is substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C5$-$C_{36}$ arylene, $C_5$-$C_{36}$ heteroarylene or is an oligomeric polyester, polycarbonate, non-PEG polyether, silicone or other oligomeric structure with appropriate linker endgroups. Certain of the $R^1$ groups may be branched or unbranched. In an embodiment, $L^1$ is a single bond, —$(CH_2)_n$—, —$(HCCH)_n$—, —O—, —S—, —SO—, —$SO_2$—, —$SO_3$—, —$OSO_2$—, —$NR^2$—, —CO—, —COO—, —OCO—, —OCOO—, —$CONR^3$—, —$NR^4CO$—, —$OCONR^5$—, —$NR^6COO$—, or —$NR^7CONR^8$—; where each of $R^2$-$R^8$ is independently hydrogen or $C_1$-$C_{10}$ alkyl; and n is an integer selected from the range of 1 to 16.

In an embodiment, $L^1$ is ester or amide (Formulas 13 and 14, respectively).

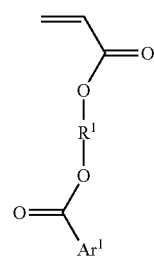

(Formula 13)

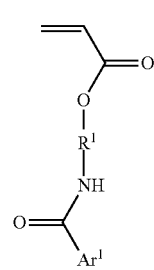

(Formula 14)

Formula 13-A illustrates one radiopaque monomer suitable for use with the invention where $Ar^1$ of Formula 13 is a $C_6$ aryl group, each of $X_1$-$X_5$ are either a radioaopaque moiety or hydrogen and n is an integer from 1 to 8. In different embodiments, at least three of $X_1$-$X_5$ are iodine or at least two of $X_1$-$X_5$ are iodine and n is an integer from 1 to 8.

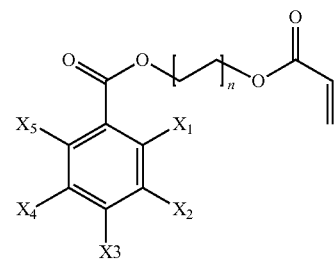

(Formula 13-A)

Formula 15 illustrates one iodinated monomer suitable for use with the invention, which comprises an acrylate end group and an iodinated $C_6$ aryl end group having 3 iodine atoms. With reference to Formula 8, $R^1$ is $C_2$ alkylene and $L^1$ is ester.

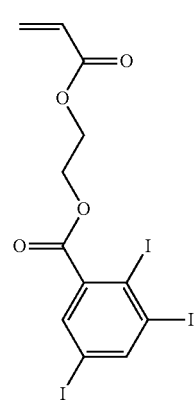

(Formula 15)

Other numbers of iodine atoms may be employed. Formulas 16 and 17 respectively illustrate monomers with four and five iodine atoms.

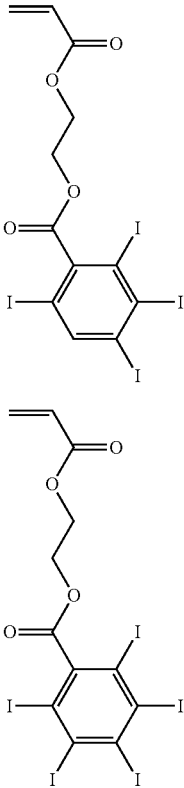

(Formula 16)

(Formula 17)

In another embodiment, $R^1$ may be unbranched unsubstituted $C_6$ alkylene, as illustrated in Formula 18.

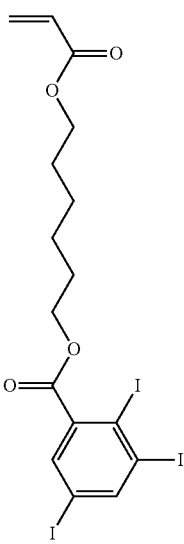

(Formula 18)

A second iodinated monomer, different from the first, may be included in the monomer mixture. This monomer may be described by the general formula shown in Formula 11.

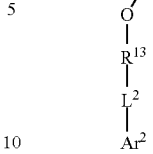

(Formula 11)

where $R^{13}$ is substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, or $C_5$-$C_{36}$ heteroarylene or is an oligomeric polyester, polycarbonate, non-PEG polyether, silicone or other oligomeric structure with appropriate linker endgroups. Certain of the $R^{13}$ groups may be branched or unbranched. In an embodiment, $L^2$ is a single bond, —(CH$_2$)$_n$—, —(HCCH)$_n$—, —O—, —S—, —SO—, —SO$_2$—, —SO$_3$—, —OSO$_2$—, —NR$^2$—, —CO—, —COO—, —OCO—, —OCOO—, —CONR$^3$—, —NR$^4$CO—, —OCONR$^5$—, —NR$^6$COO—, or —NR$^7$CONR$^8$—; Ar$^2$ is a $C_5$-$C_{30}$ aryl or $C_5$-$C_{30}$ heteroaryl that is substituted with three or more I, Br or Bi atoms; and each of $R^2$-$R^8$ is independently hydrogen or $C_1$-$C_{10}$ alkyl with n being an integer selected from the range of 1 to 10 and $R^{13}$ being other than $R^1$. In an embodiment, $L^2$ is ester or amide.

In an embodiment, use of two iodinated monomers with related but different chemical structures can aid in suppressing crystallinity in the resulting polymer. In an embodiment, both iodinated monomers comprise acrylate end groups, aliphatic $C_2$-$C_{36}$ alkylene R groups (e.g. $R^1$ in Formula 8 and $R^{13}$ in Formula 11), ester L groups (e.g. $L^1$ in Formula 8 and $L^2$ in Formula 11) and $C_6$ aryl Ar groups (e.g. Ar$^1$ in Formula 8 and Ar$^2$ in Formula 11), but vary in the length of the aliphatic R groups and/or the number or arrangement of iodine atoms on the aryl ring.

The crosslinking monomer, in combination with the other monomers in the mixture, allows formation of a crosslinked network. The structure and amount of crosslinker(s) in the monomer mixture may be selected to provide a sufficiently high crosslink density to achieve the desired modulus in the composition. In different embodiments, the molecular weight of the crosslinker is in the range from 200 to 1000, 200 to 2000 or 200-5000, or any other useful molecular weight range. Blends of crosslinkers can allow shorter and longer crosslinkers to be used together.

In an embodiment, the multifunctional crosslinking monomer comprises a plurality of acrylate polymerizable groups. In another embodiment, the multifunctional iodinated monomer comprises a plurality of styrene, acrylamide, or methacrylamide polymerizable groups.

In an embodiment, the crosslinking monomer may be classified as "hydrophobic". In an embodiment, a hydrophobic monomer may be defined as being insoluble in water. In an embodiment, the crosslinking monomer is less soluble in water than a poly(ethylene glycol) di(meth)acrylate of comparable molecular weight.

In an embodiment, the crosslinking monomer is a bifunctional monomer and the polymerizable groups are end groups. In an embodiment, the polymerizable groups are linked by an aliphatic hydrocarbon moiety. Other forms of linkage may also be used. For example, the monomer may include a linkage containing a modified Bisphenol A moiety. Formula 19 illustrates a Bisphenol A propoxylate with acrylate endcaps. In addition, linkages of other single segments, or monomers comprising polyester, epoxy, silicone, or other short polymer segments capped by acrylate or other polymerizable groups may be used. In another embodiment, the linkage may be derived from a dimer alcohol, which may be capped by acrylate endgroups. In another embodiment, the linkage may be derived from poly(dimethylsiloxane) (PDMS) and may be combined with acrylate endcaps to form poly(dimethylsiloxane) diacrylate. The linkage may also be a dimer acid converted to acid chloride and capped with a hydroxyl-functional monomer, such as the hydroxyethyl-acrylate that is now used to cap 2,3,5-triiodobenzoic acid.

(Formula 19)

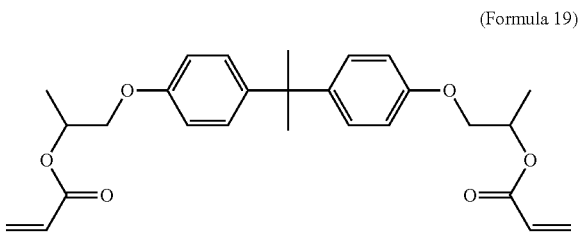 [SMILES: C=CC(=O)OC(C)COc1ccc(C(C)(C)c2ccc(OCC(C)OC(=O)C=C)cc2)cc1]

In an embodiment, the linkage between the polymerizable end groups is not poly(ethylene glycol).

In an embodiment, the crosslinker monomer has the general structure according to Formula 9

(Formula 9)

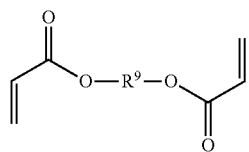

where $R^9$ is substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, an oligomeric polyester, an oligomeric polycarbonate, an oligomeric polyurethane, (Formula 3)

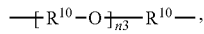

(Formula 4)

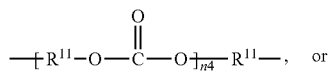

or (Formula 4-A)

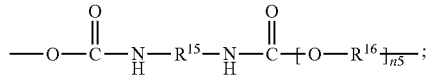

wherein $R^{10}$ is $C_4$-$C_{20}$ alkylene and $n_3$ is an integer from 1 to 50 or wherein $R^{11}$ is $C_3$-$C_{20}$ alkylene and $n_4$ is an integer from 1 to 50; where $R^{15}$ is aliphatic group, substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, aromatic group, polyalkyl siloxane group, polyether group, polyester group, polycarbonate group or a combination of linear or branched aliphatic groups and aromatic groups and $R^{16}$ is ether group, polyalkyl siloxane group, polyether group, polyester group, polycarbonate group $C_3$-$C_{20}$ alkylene, aliphatic group, substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, or aromatic group, or a combination of aliphatic groups and aromatic groups and $n_5$ is an integer from 1 to 50.

In an embodiment, $R^9$ is unsubstituted unbranched $C_4$-$C_{12}$ alkylene or an unsubstituted unbranched $C_{10}$ alkylene.

In an embodiment, the crosslinker monomer is an oligomeric polyester, an oligomeric polycarbonate or an oligomeric polyurethane. In an embodiment, the molecular weight of the oligomer is less than 1000. In another embodiment, the crosslinker monomer comprises a polycondensate of one or more compounds selected from the group consisting of: diacid chloride, diol, diisocyanate, bis-chloroformate. In an embodiment, when the structure of the crosslinker molecule is according to Formula 9, the number of atoms in $R^9$ may be from 10 to 100. In another embodiment, a polyol having more than two OH groups can be condensed with diacid chloride, diisocyanate or bis-chloroformate. The compounds used to form the polycondensate can be linear or branched aliphatic, cycloaliphatic, partially cycloaliphatic or partially aromatic. For example, polycarbonate oligomers can be formed through condensation of bis-chloroformates with diols or other polyols, polyester oligomers can be formed through condensation of diacid chlorides and diols or other polyols, and polyurethane oligomers can be formed through condensation of diisocyanates and diols or other polyols. The polycondensates can be end-capped with acrylate using acryloyl chloride (with diol precursor) or 2-hydroxyethyl acrylate (with diacid chloride precursor).

In an embodiment, the oligomeric crosslinker is a poly($C_2$-$C_{36}$ carbonate) diacrylate. Formula 9A illustrates a polycarbonate diacrylate crosslinker. In an embodiment, $R^9$ is according to formula 4 with $R^{11}$ being an unsubstituted unbranched $C_3$ alkylene, resulting in poly(trimethylene carbonate) (PTMC) diacrylate; an example is given in Figure 9-B. A poly(hexamethylene carbonate) diacrylate (PHMCDA) crosslinker can also be used; an example is given in Figure 9-C.

(Formula 9-A)

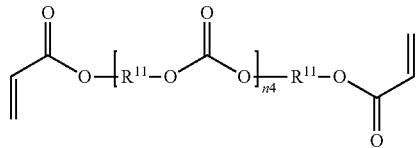

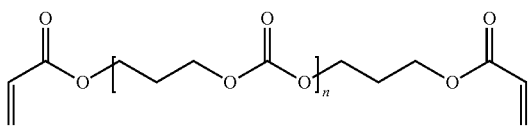
(Formula 9-B)

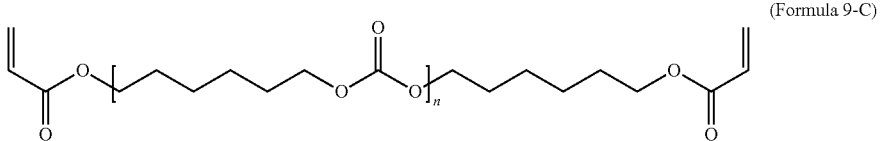
(Formula 9-C)

In an embodiment, the crosslinker monomer is a non-PEG polyether oligomer, an example of which is illustrated in Formula 3. In an embodiment, $R^9$ is according to formula 3, with $R^{10}$ being an unsubstituted unbranched $C_4$ alkylene, resulting in a polytetrahydrofuran (poly(THF))diacrylate.

A second crosslinking monomer, different from the first, may be included in the monomer mixture. This second crosslinking monomer may be a bifunctional monomer whose polymerizable endgroups are linked by linkages similar to those described for the first crosslinking monomer. In an embodiment, this second crosslinking monomer can be described by the general formula:

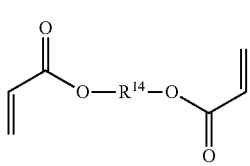
(Formula 12)

where $R^{14}$ is substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, an oligomeric polyester, an oligomeric polycarbonate, an oligomeric polyurethane,

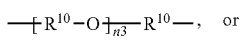
(Formula 3)

or

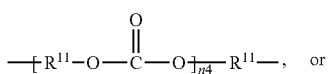
(Formula 4)

or

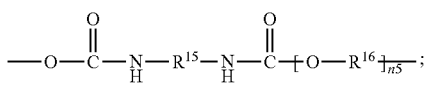
(Formula 4-A)

wherein $R^{10}$ is $C_4$-$C_{20}$ alkylene and $n_3$ is an integer from 1 to 50 or
wherein $R^{11}$ is $C_3$-$C_{20}$ alkylene and $n_4$ is an integer from 1 to 50
and $R^{14}$ is other than $R^9$ and where $R^{15}$ is aliphatic group, substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, aromatic group, polyalkyl siloxane group, polyether group, polyester group, polycarbonate group or a combination of linear or branched aliphatic groups and aromatic groups and $R^{16}$ is ether group, polyalkyl siloxane group, polyether group, polyester group, polycarbonate group, $C_3$-$C_{20}$ alkylene, aliphatic group, substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, or aromatic group, or a combination of aliphatic groups and aromatic groups and $n_5$ is an integer from 1 to 50.

Similarly to the first crosslinker, in different embodiments $R^{14}$ is unsubstituted unbranched $C_4$-$C_{12}$ alkylene, unsubstituted unbranched $C_{10}$ alkylene, $C_2$-$C_{36}$ carbonate or $C_4$-$C_{20}$ ether.

An optional monofunctional non-radiopaque co-monomer can be used to adjust the properties of the polymer. For example, the co-monomer can be used to modify the glass transition temperature (Tg) of the polymer. As another example, the co-monomer can be selected to assist in system compatibilization.

In an embodiment, the non-radiopaque co-monomer is a vinyl monomer. A wide range of commercially-available vinyl monomers can be utilized, including but not limited to butyl acrylate, which imparts a Tg value near −40° C. Such a low glass transition temperature can help to offset the typically higher Tg contribution of radiopaque monomer and crosslinkers having relatively low molecular weight values. The amenability of a wide cross section of vinyl monomers to polymerization or copolymerization by a free radical mechanism facilitates access to useful structure-property modifications.

In an embodiment, the monofunctional non-radiopaque co-monomer comprises an acrylate polymerizable group. In another embodiment, the monofunctional co-monomer comprises a styrene, acrylamide, or methacrylamide polymerizable group. In an embodiment, the polymerizable group is an end group. Though styrene monomers typically do not polymerize as aggressively and to as high a conversion as acrylates, in copolymerization reactions with acrylates styrene monomers propagate more readily and can be used to good advantage where required. In different embodiments, the amount of comonomer may be from 2.5-90 wt %, 5-80 wt %, 10-80 wt %, 20-90 wt %, 2.5-10 wt %, 5-50 wt %, 5-25 wt %, 25-50 wt %, 50-80 wt %, 10-50 wt %, 20-50 wt %, or 10-70 wt %, or any other range producing a functional end-product. In an embodiment, the comonomer is not present.

In an embodiment, the non-radiopaque co-monomer may be described by the general formula of Formula 10:

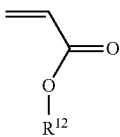
(Formula 10)

where $R^{12}$ is $C_2$ to $C_{36}$ alkyl, $C_2$-$C_{10}$ alkyl or $C_4$ alkyl. The alkyl group may be branched or unbranched.

In an embodiment, provided is a polymer composition comprising a crosslinked network, the network comprising:
a) a first repeating unit having one of Formula 1, 1-A, 1-B or 1-C:

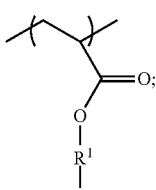
(Formula 1)

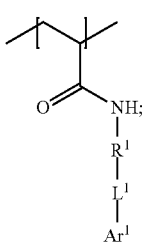
(Formula 1-A)

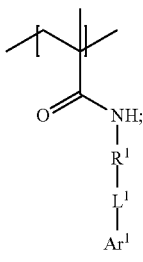
(Formula 1-B)

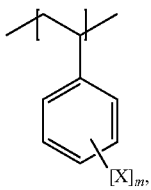
(Formula 1-C)

wherein X is Br or I; m is an integer from 3-5; $R^1$ is substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, or $C_5$-$C_{36}$ heteroarylene; $L^1$ is a single bond, —(CH$_2$)$_n$—, —(HCCH)$_n$—, —O—, —S—, —SO—, —SO$_2$—, —SO$_3$—, —OSO$_2$—, —NR$^2$—, —CO—, —COO—, —OCO—, —OCOO—, —CONR$^3$—, —NR$^4$CO—, —OCONR$^5$—, —NR$^6$COO—, or —NR$^7$CONR$^8$—; $Ar^1$ is a $C_5$-$C_{30}$ aryl or $C_5$-$C_{30}$ heteroaryl that is substituted with three or more I, Br or Bi atoms; each of $R^2$-$R^8$ is independently hydrogen or $C_1$-$C_{10}$ alkyl; and n is an integer selected from the range of 1 to 16;

b) a second repeating unit having the formula:

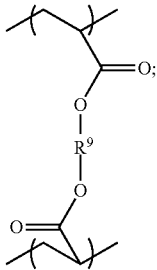
(Formula 2)

wherein $R^9$ is substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, an oligomeric polyester, an oligomeric polycarbonate, an oligomeric polyurethane,

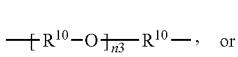
(Formula 3)

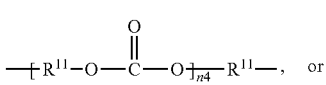
(Formula 4)

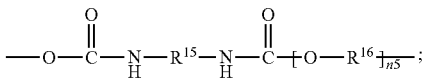
(Formula 4-A)

wherein $R^{10}$ is $C_4$-$C_{20}$ alkylene and $n_3$ is an integer from 1 to 50 or
wherein $R^{11}$ is $C_3$-$C_{20}$ alkylene and $n_4$ is an integer from 1 to 50 and where $R^{15}$ is aliphatic group, substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, aromatic group, polyalkyl siloxane group, polyether group, polyester group, polycarbonate group or a combination of linear or branched aliphatic groups and aromatic groups and $R^{16}$ is ether group, polyalkyl siloxane group, polyether group, polyester group, polycarbonate group, $C_3$-$C_{20}$ alkylene, aliphatic group, substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, or aromatic group, or a combination of aliphatic groups and aromatic groups and $n_5$ is an integer from 1 to 50.

In an embodiment, provided is a polymer composition comprising a first repeating unit as described herein, a second repeating unit as described herein and one or more third repeating units having the formula of the second repeating unit or according to Formula 5

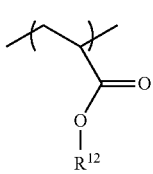
(Formula 5)

where $R^{12}$ is $C_2$ to $C_{36}$ alkyl.

In an embodiment, the number of repeating units described or shown herein is not specifically limited, but is rather any number that is functionally feasible, that is, can be synthesized and has the desired use in the desired compositions, compounds, methods and devices. As a non-limiting example, the number of repeating units in the first repeating unit is between 1 and 10,000 in an embodiment. As a non-limiting example, the number of repeating units in the second repeating unit is between 5 and 10,000 in an embodiment.

In an embodiment, provided is a polymer composition comprising a crosslinked network, the network comprising:
(a) a first repeating unit having the repeating unit of an acrylate ester of 2,3,5-triiodobenzoic acid;
(b) a second repeating unit having the repeating unit of a polycarbonate diacrylate;
(c) a third repeating unit having the repeating unit of a diol diacrylate, such as decanediol-diacrylate.

In an embodiment, a second repeating unit is derived from a polycarbonate diacrylate and a third repeating unit is derived from a diol-diacrylate. In an embodiment of this aspect, the weight percentage of the first repeating unit is from 10-90 wt %, the weight percentage of the second repeating unit is from 5 to 90 wt % and the weight percentage of the third repeating unit is from 0 to 75 wt %. In an embodiment of this aspect, the weight percentage of the first repeating unit is from 20-90 wt %, the weight percentage of the second repeating unit is from 5 to 75 wt % and the weight percentage of the third repeating unit is from 5 to 75 wt %. In an embodiment of this aspect, the weight percentage of the first repeating unit is from 50-85 wt %, the weight percentage of the second repeating unit is from 10 to 55 wt % and the weight percentage of the third repeating unit is from 0 to 55 wt %. In an embodiment of this aspect, the weight percentage of the first repeating unit is from 30-75 wt %, the weight percentage of the second repeating unit is from 10 to 50 wt % and the weight percentage of the third repeating unit is from 10 to 50 wt %. As is recognized, any permutation of the components described that produces a functional final product can be used, even if not specifically described herein. In an embodiment of this aspect, the weight percentage of the first repeating unit is from 10-50 wt %, the weight percentage of the second repeating unit is from 10 to 50 wt % and the weight percentage of the third repeating unit is from 10 to 50 wt %. In an embodiment of this aspect, the weight percentage of the first repeating unit is from 10-90 wt %, the weight percentage of the second repeating unit is from 90 to 10 wt %. It is understood that all lower, intermediate and higher values and ranges are included to the same extent as if they were included separately.

In an embodiment, the polymer composition further comprises a metal marker band. In an embodiment of this aspect, the metal marker band comprises platinum-iridium or gold.

In an embodiment, polymer composition comprises a first repeating unit as described herein, and second and third repeating units comprising an acrylate moiety. In an embodiment of this aspect, the second and third repeating units are derived from n-butyl acrylate and ethyl-hexyl-acrylate.

In an embodiment, the amount of the first repeating unit is from 5-90 wt % of the total weight of the composition. In an embodiment, the amount of the first repeating unit is from 15-90 wt % of the total weight of the composition. In an embodiment, the amount of the first repeating unit is at least 50% of the total weight of the composition. In an embodiment, the amount of the first repeating unit is at most 50% of the total weight of the composition. In an embodiment, the amount of the first repeating unit is from 15-70 wt % of the total weight of the composition. In an embodiment, the amount of the first repeating unit is from 15-40 wt %, 15-35 wt %, or 20-30 wt % of the total weight of the composition. In an embodiment, the amount of the first repeating unit is from 40-70 wt % or 40-80 wt % of the total weight of the composition. In an embodiment, the amount of the second repeating unit is below 80 wt % of the total weight of the composition. In an embodiment, the amount of the second repeating unit is at most 50 wt % of the total weight of the composition. In an embodiment, the amount of the second repeating unit is at least 50 wt % of the total weight of the composition. In an embodiment, the amount of the second repeating unit is from 65-85 wt % or 70-80 wt % of the total weight of the composition. In an embodiment, the amount of the second repeating unit is at most 40 wt % of the total weight of the composition. In an embodiment, the amount of the first repeating unit is from 40 wt %-70 wt % of the network, the amount of the second repeating unit is from 10 wt %-60 wt % of the network, and the amount of the third repeating unit is from 20 wt %-50 wt % of the network, with the total amounts of the first, second and third repeating units being 100 wt %. Any permutation of the components described where the total amounts of the second and third repeating units is 100 wt % can be used and is intended to be described to the same extent as if specifically described.

In an embodiment, provided is a polymer composition network as described herein, the network further comprising a repeating unit having the formula:

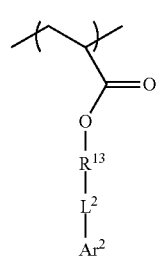

(Formula 6)

wherein $R^{13}$ is substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, or $C_5$-$C_{36}$ heteroarylene; $L^2$ is a single bond, —$(CH_2)_n$—, —$(HCCH)_n$—, —O—, —S—, —SO—, —$SO_2$—, —$SO_3$—, —$OSO_2$—, —$NR^2$—, —CO—, —COO—, —OCO—, —OCOO—, —$CONR^3$—, —$NR^4CO$—, —$OCONR^5$—, —$NR^6COO$—, or —$NR^7CONR^8$—; $Ar^2$ is a $C_5$-$C_{30}$ aryl or $C_5$-$C_{30}$ heteroaryl that is substituted with three or more I, Br or Bi atoms; and each of $R^2$-$R^8$ is independently hydrogen or $C_1$-$C_{10}$ alkyl; n is an integer selected from the range of 1 to 16 and $R^{13}$ is other than $R^1$.

In an embodiment, provided is a polymer composition network as described herein, the network further comprising a repeating unit having the formula:

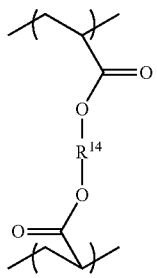

(Formula 7)

where $R^{14}$ is substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, an oligomeric polyester, an oligomeric polycarbonate, an oligomeric polyurethane,

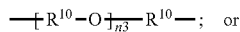

(Formula 3)

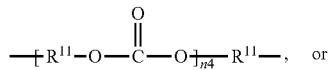

(Formula 4)

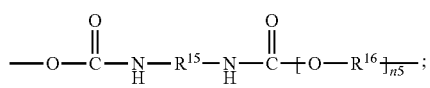

(Formula 4-A)

wherein $R^{10}$ is $C_4$-$C_{20}$ alkylene and $n_3$ is an integer from 1 to 50 or wherein $R^{11}$ is $C_3$-$C_{20}$ alkylene and $n_4$ is an integer from 1 to 50, and $R^{14}$ is other than $R^9$; and wherein $R^{15}$ is aliphatic group, substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, aromatic group, polyalkyl siloxane group, polyether group, polyester group, polycarbonate group or a combination of linear or branched aliphatic groups and aromatic groups and $R^{16}$ is ether group, polyalkyl siloxane group, polyether group, polyester group, polycarbonate group, $C_3$-$C_{20}$ alkylene, aliphatic group, substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, or aromatic group, or a combination of aliphatic groups and aromatic groups and $n_5$ is an integer from 1 to 50.

In an embodiment, the composition as described herein is substantially amorphous. In an embodiment, the composition as described herein is a shape memory polymer composition. In an embodiment, provided is a polymer composition network comprising repeating units derived from a monofunctional iodinated monomer comprising a styrene, acrylamide or methacrylamide polymerizable group.

In an embodiment, provided is a polymer composition comprising a crosslinked network formed by polymerization of a monomer mixture comprising a) a first monomer having the general structure according to Formula 8, 8-A, 8-B or 8-C:

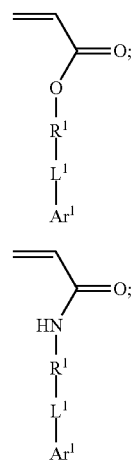

(Formula 8)

(Formula 8-A)

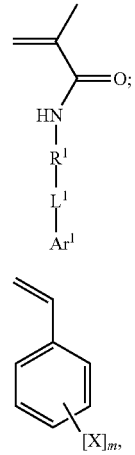

(Formula 8-B)

(Formula 8-C)

wherein X is Br or I; m is an integer from 3-5; wherein $R^1$ is substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, or $C_5$-$C_{36}$ heteroarylene; $L^1$ is a single bond, $-(CH_2)_n-$, $-(HCCH)_n-$, $-O-$, $-S-$, $-SO-$, $-SO_2-$, $-SO_3-$, $-OSO_2-$, $-NR^2-$, $-CO-$, $-COO-$, $-OCO-$, $-OCOO-$, $-CONR^3-$, $-NR^4CO-$, $-OCONR^5-$, $-NR^6COO-$, or $-NR^7CONR^8-$;

$Ar^1$ is a $C_5$-$C_{30}$ aryl or $C_5$-$C_{30}$ heteroaryl that is substituted with three or more I, Br or Bi atoms I; and each of $R^2$-$R^8$ is independently hydrogen or $C_1$-$C_{10}$ alkyl;

n is an integer selected from the range of 1 to 16;

b) a second monomer having the general structure according to Formula 9

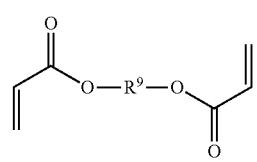

(Formula 9)

$R^9$ is substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, an oligomeric polyester, an oligomeric polycarbonate, an oligomeric polyurethane,

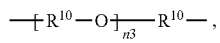 (Formula 3)

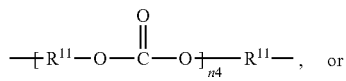 (Formula 4)

or (Formula 4-A)

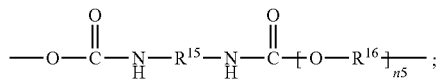

wherein $R^{10}$ is $C_4$-$C_{20}$ alkylene and $n_3$ is an integer from 1 to 50 or
wherein $R^{11}$ is $C_3$-$C_{20}$ alkylene and $n_4$ is an integer from 1 to 50 and where $R^{15}$ is aliphatic group, substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, aromatic group, polyalkyl siloxane group, polyether group, polyester group, polycarbonate group or a combination of linear or branched aliphatic groups and aromatic groups and $R^{16}$ is ether group, polyalkyl siloxane group, polyether group, polyester group, polycarbonate group, $C_3$-$C_{20}$ alkylene, aliphatic group, substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, or aromatic group, or a combination of aliphatic groups and aromatic groups and $n_5$ is an integer from 1 to 50.

In an embodiment, the mixture further comprises a third monomer having the general structure according to Formula 10

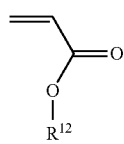 (Formula 10)

where $R^{12}$ is $C_2$ to $C_{36}$ alkyl.

In an embodiment, provided is a method for making a polymer composition comprising a crosslinked network, the method comprising the steps of: a) forming a monomer mixture comprising a first monomer as described herein, a second monomer as described herein, and a free radical initiator; and b) polymerizing the monomer mixture. In an embodiment, the monomer mixture is substantially homogeneous.

Also provided is a radiopaque polymer device comprising a polymer composition as described herein. In an embodiment, the device is useful for purposes of an indwelling, permanent implant to provide the function of: opening, or maintaining an open anatomical lumen; closing an anatomical lumen, either partially as a valve, or complete lumen occlusion for any physiological fluid or gas flow or for a applied therapeutic fluid or gas flow; support of an anatomical structure to assist in therapeutic restoration of an organ, vascular, digestive, excrement, or airway function; support of an anatomical structure to assist in therapeutic restoration of an orthopaedic, maxillofacial, spinal, joint or other skeletal or function; or to support hemostasis by covering an area after tissue dissection or resection, a patch, such as for hemostasis of the liver, or other organ. In an embodiment, the device is useful for diagnostic or therapeutic instrument or device to provide the function of: a) a catheter for the purposes of accessing an anatomical location; delivering another device and/or therapeutic agent; or controlling the access or delivery of another device and/or therapeutic agent; or b) a temporarily indwelling device to provide a limited time therapeutic benefit, such as a vena cava filter that is placed in a vessel, left indwelling for a period of time, for example to capture blood clots, and subsequently removed when the therapeutic period is completed.

In an embodiment, the amount of the radiopaque monomer in the monomer mixture is at least 5-10 wt %. As used herein, the wt % of radiopaque monomer in the mixture may be the 100*(the weight of the radiopaque monomer/the weight of the mixture). In an embodiment, the amount of the radiopaque monomer is from 15 wt % to 90 wt % of the monomer mixture. In different embodiments, the amount of the radiopaque monomer is from 15 wt % to 40 wt %, 15-35 wt %, or 20-30 wt % of the monomer mixture. In an embodiment, the amount of the radiopaque monomer in the monomer mixture is at least 20 wt %. In an embodiment, the amount of the radiopaque monomer in the monomer mixture is at least 25 wt %. In an embodiment, the amount of the radiopaque monomer in the monomer mixture is at least 30 wt %. In another embodiment, the amount of the radiopaque monomer is from 40-70 wt % or 40-80 wt % of the monomer mixture. In an embodiment, the amount of the radiopaque monomer in the monomer mixture is at least 50 wt % and can even reach 100%. In an embodiment, the amount of the crosslinker in the monomer mixture is less than or equal to 80 wt %. In an embodiment, the amount of the crosslinker(s) in the monomer mixture is less than or equal to 90 wt %. In different embodiments, the amount of the crosslinker(s) in the monomer mixture may be 60-85 wt %, 65-85%, 70-80 wt % or less than or equal to 75 wt % of the monomer mixture. In another embodiment, the monomer mixture comprises 40%-70 wt % of radiopaque monomer(s), 10-60 wt % crosslinker, and 20-50 wt % added co-monomer with the total amount including photoinitiator or other free radical initiator being 100 wt %. In an embodiment, the amount of initiator is less than 1 wt %. In an embodiment, the monomer mixture comprises at least 60 wt % radiopaque monomer(s), and less than or equal to 40 wt % crosslinker(s). In an embodiment, the monomer mixture comprises at least 50 wt % radiopaque monomer(s), and less 50 wt % crosslinker(s). As will be understood, any permutation of the components that produces a functional compound or composition can be used.

A wide range of free radical initiating systems may be used for polymerization. In different embodiments, the initiator may be a photoinitiator, a thermal initiator or a redox (reduction oxidation) initiator. Photoinitiating systems are particularly useful, provided that a photoinitiator is chosen that does not require wavelengths of light that are absorbed excessively by the base monomer ingredients of the formulation. Irgacure 819 (Ciba (BASF), Bis(2,4,6-trimethylbenzoyl)-phenylphosphineoxide) is one example of a photoinitiator that has been found to be particularly useful for the curing system.

Photopolymerization occurs when monomer solution is exposed to light of sufficient power and of a wavelength capable of initiating polymerization. The wavelengths and power of light useful to initiate polymerization depends on the initiator used. Light used in the invention includes any wavelength and power capable of initiating polymerization. Preferred wavelengths of light include ultraviolet. In different embodiments, the light source primarily provides light having a wavelength from 200 to 500 nm or from 200 to 400 nm. In an embodiment, 1-100 mW/cm² of 200-500 nm light is applied for a time from 10 sec to 60 mins. Any suitable source may be used, including laser sources. The source may be filtered to the desired wavelength band. The source may be broadband or narrowband, or a combination. The light source may provide continuous or pulsed light during the process.

Thermal initiating systems, with low-temperature or high-temperature initiators, common examples being benzoyl peroxide and azobisisobutyronitrile (AIBN), are also useful in situations where a particularly large or irregularly-shaped object that is difficult to illuminate uniformly is to be prepared. Also of use in the latter scenario are free radical initiating systems that produce free radicals by any type of redox reaction, such as the Fenton system involving ferrous salts with tert-butyl hydroperoxide, or other metal-organic, organic such as triethylamine+hydroperoxides, or photo-organic redox systems, an example of the latter being the Eosin-Y+triethanolamine visible light initiating system.

A number of pseudo-living free radical polymerization systems, some of which are capable of producing polymers with narrower molecular weight distributions than conventional free radical polymerizations, are also described in the art and can be amenable to production of crosslinker segments for SMPs or for SMP curing. For example, styrene monomers that polymerize to low conversion in a conventional system may be driven to high conversion in a pseudo-living system. These pseudo-living systems typically involve variable combinations of reversible chain propagation-termination and/or chain transfer steps. "Living" free radical polymerizations known to the art include, but are not limited to, NMP, RAFT, and ATRP.

Additionally, any other type of non-conventional free radical polymerization process, whether pseudo-living or not, that produces free radicals capable of initiating polymerization of the radiopaque and non-radiopaque monomers and crosslinkers comprising the SMPs of this invention, fall within the scope of potential initiating-polymerization methods. These and other free radical initiating systems are conceivable and known to those skilled in the art.

In embodiments, examples of the useful initiating systems include anionic, cationic, free radical polymerizations that are non-living, pseudo-living or living as well as Ziegler-Natta and olefin metathesis. The use of these systems is known in the art. In an embodiment, these systems are useful if a prepolymerized segment is at least difunctional and has hydroxyl or other groups known in the art which can be used to attach polymerizable groups, including acrylate groups in an embodiment.

In an embodiment, some or all of the components of the monomer mixture are combined at a temperature greater than ambient temperature. In different embodiments, the initiator may be added at the same time as the monomer components or added just prior to or at the time of molding. In another embodiment where a thermal initiator is used, the monomer mixture ingredients may be divided into two parts; wherein the high storage temperature ingredients are in Part A, and the lower storage temperature ingredients are in Part B. The thermal initiator may be added to the lower storage temperature ingredients in Part B at a storage temperature that is below the initiator's polymerization temperature. In an embodiment, forming the monomer mixture (or a portion of the monomer mixture) at greater than ambient temperature can assist in maintaining solubility of the monomer mixture components, thereby enabling formation of a homogenous mixture.

In an embodiment, the monomer mixture is held at a temperature greater than ambient temperature during free radical polymerization. In an embodiment, the monomer mixture is held a temperature between 65° C. and 150° C. or from 65° C. and 100° C. during the polymerization step. In an embodiment, a pre-cure step is performed in a vacuum environment. In separate embodiments, the curing step is performed using free radical, anionic, cationic, Diels-alder, thiol-ene, polycondensation, or other mechanisms known in the art. During molding, pressure may be applied during polymerization to ensure mold filling.

In an embodiment, an additional curing or heat treatment step is employed after the polymerization step (e.g. after photopolymerization). In an embodiment, the cured parts are removed from the mold and then undergo additional curing operations through exposure to elevated temperatures. In an embodiment, the curing temperature is from 50° C. and 150° C. and the curing time from 5 seconds to 60 minutes during this additional step.

In different embodiments, the amount of functional group conversion is at least 30%, 40%, 50%, 60%, 70%, 80% or 90% or higher. In an embodiment, the amount of extractables is less than or equal to 1% or less than or equal to 0.5%. In an embodiment, the amount of extractables is less than or equal to 5%. In an embodiment, the amount of extractables is less than or equal to 3%. In an embodiment, the amount of extractables is less than or equal to 2%. In an embodiment, the amount of extractables is determined by isopropanol extraction.

In an embodiment, the cross-linked polymer network comprises a repeating unit derived from a monofunctional iodinated monomer and a repeating unit derived from a multifunctional non-iodinated crosslinking monomer. In an embodiment, the network may also comprise a repeating unit derived from a non-iodinated monofunctional co-monomer. In an embodiment, the repeating unit derived from this co-monomer may be described by the general formula of Formula 5:

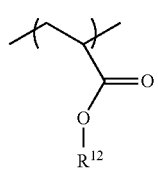

(Formula 5)

In an embodiment $R^{12}$ is $C_2$ to $C_{36}$ alkyl. $R^{12}$ may be branched or unbranched.

In another embodiment, the network may further comprise a repeating unit derived from an additional iodinated monomer. This repeating unit may be described by the general formula of Formula 6:

(Formula 6)

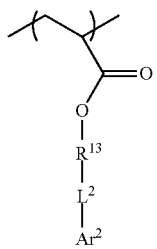

In an embodiment, $R^{13}$ is substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, or $C_5$-$C_{36}$ heteroarylene; $L^2$ is a single bond, —$(CH_2)_n$—, —(HCCH)$_n$—, —O—, —S—, —SO—, —SO$_2$—, —SO$_3$—, —OSO$_2$—, —NR$^2$—, —CO—, —COO—, —OCO—, —OCOO—, —CONR$^3$—, —NR$^4$CO—, —OCONR$^5$—, —NR$^6$COO—, or —NR$^7$CONR$^8$—;
$Ar^2$ is a $C_5$-$C_{30}$ aryl or $C_5$-$C_{30}$ heteroaryl that is substituted with three or more I, Br or Bi atoms; and
each of $R^2$-$R^8$ is independently hydrogen or $C_1$-$C_{10}$ alkyl;
n is an integer selected from the range of 1 to 16
and $R^{13}$ is other than R.

In another embodiment, the network may further comprise a repeating unit derived from an additional crosslinking monomer. This repeating unit may be described by the general formula:

(Formula 7)

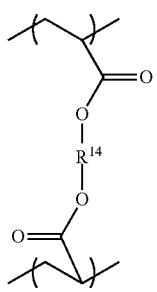

In an embodiment, $R^{14}$ is substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, an oligomeric polyester, an oligomeric polycarbonate, an oligomeric polyurethane,

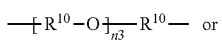 (Formula 3)

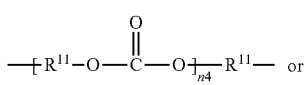 (Formula 4)

(Formula 4-A)

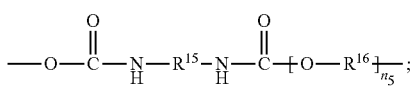

wherein $R^{10}$ is $C_4$-$C_{20}$ alkylene and $n_3$ is an integer from 1 to 50 or
wherein $R^{11}$ is $C_3$-$C_{20}$ alkylene and $n_4$ is an integer from 1 to 50.

and $R^{14}$ is other than $R^9$ and wherein $R^{15}$ is aliphatic group, substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, aromatic group, polyalkyl siloxane group, polyether group, polyester group, polycarbonate group or a combination of linear or branched aliphatic groups and aromatic groups and $R^{16}$ is ether group, polyalkyl siloxane group, polyether group, polyester group, polycarbonate group, $C_3$-$C_{20}$ alkylene, aliphatic group, substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, or aromatic group, or a combination of aliphatic groups and aromatic groups and $n_5$ is an integer from 1 to 50.

As used herein, a crystalline material displays long range order. The crystallinity of polymers is characterized by their degree of crystallinity, or weight or volume fraction of crystalline material in the sample ranging from zero for a completely non-crystalline polymer to one for a theoretical completely crystalline polymer.

If a polymer is semicrystalline, shape change can be hindered and slowed, and performance of devices incorporating the polymer can become clinically unacceptable. In an embodiment, the polymer compositions of the invention are considered substantially amorphous. As used herein, substantially amorphous is defined as the absence of crystalline features as detected by differential scanning calorimetry (DSC), or by inconsistency and lack of reproducibility in mechanical tensile test results, e.g. stress-strain curve at a fixed temperature. In an embodiment, lack of reproducibility may be indicated by reproducibility of less than 95% at 95% confidence interval. A substantially amorphous polymer may incorporate relatively small amounts of crystallinity. As is typical of amorphous polymers, the substantially amorphous polymer compositions of the invention show a transition from a glassy state to a rubbery state over a glass transition temperature range. Crystallinity can be reduced or eliminated by reducing the concentration of specific monomers that enhance this condition, and/or by introducing dissimilar structures to ensure that the polymer's molecular structure doesn't align during polymerization to result in crystallinity.

In an embodiment, the monomers (including crosslinking monomers) used to form the radiopaque polymer are selected to assure compatibility (e.g. homogeneity after polymerization). In an embodiment, the radiopaque polymer is sufficiently homogenous in terms of solid-phase compatibility of the polymerized units and in the sufficiently random incorporation of units throughout polymerization to obtain the desired performance characteristics. Phase incompatibility can lead to voids in the polymer morphology. Voids in the polymer matrix compromise mechanical performance and can lead to uptake of water and other fluids that displace the generated void volume, even when the incompatible phases are hydrophobic or even "water-repellant." Excessively non-random incorporation of comonomers, especially diacrylate or other polyacrylate crosslinkers, as polymerization proceeds from low conversion to high conversion can lead to a non-uniform crosslink density, with regions of higher (brittle) and lower (rubbery) crosslink density.

In an embodiment, the radiopaque polymer is homogenous enough that repeatable results (95% reproducible data at 95% confidence interval) can be obtained in a simple ultimate tensile test at a fixed temperature. In an embodiment, homogeneity of the polymer may be improved by selection of the components of the monomer solution to reduce phase separation in the liquid or solid state. In addition, the monomer components and polymerization technique may be selected to facilitate random incorporation of monomer and crosslinker groups by free radical polymerization during the cure. In an embodiment, the same type of polymerizable groups is present in each of the monomers. For example, for monomers (and crosslinking monomers) having acrylate polymerizable groups and aliphatic hydrocarbon linkers, the inductive effect exerted upon the acrylate group by the typically aliphatic linker attachments is expected to be similar.

In many applications, biodurability can be defined as durability for the period of time necessary to assure that the body has overcome the need of the device's function, e.g. a fallopian tube occlusion device that relies upon scar tissue formation to close the lumen no longer needs the device to generate scar tissue once the lumen is fully closed. If that period of time is 90 days, for example, then the biodurable life of the device can be this value plus a suitable safety factor used in the design. Biodurability then is the ability of the device, and its material, to withstand the environmental challenges at its location of placement in the body, e.g. if in the bloodstream, it must withstand a bloody environment. In an embodiment, the radiopaque polymer is not biodegradable within the desired lifetime of the medical device. In another embodiment, the radiopaque polymer is not biodegradable within three years. In an embodiment, the non-biodegradable polymer does not include aromatic groups other than those present in naturally occurring amino acid. In an embodiment, the non-biodegradable polymer does not contain esters that are readily hydrolyzed at physiological pH and temperature.

For almost all locations within the body, one of the several primary mechanisms of degradation can be caused by absorption of water or moisture. Whether the environment contains interstitial fluids, blood, saliva, urine, bile, intracranial fluid, etc., these environments are aqueous based. If the device or its material absorbs water, the material properties and device dimensions can change due to swelling, or the device function can be affected, such as the autogenesis of an errant electrical path, or the material properties can degrade causing the device to weaken or break apart. Therefore a primary consideration for biodurability of an implanted device is the device and all of its material's ability to not absorb water.

In an embodiment, water uptake, or water absorption, can change the device's characteristics or detrimentally affect the device's performance over its intended life. In an embodiment, medical devices fabricated from the polymers of the invention will exhibit minimal water uptake. The water uptake can be measured over a test period equivalent to the lifetime or the device or can be measured over a shorter screening period. In an embodiment, the extent of water uptake is <1% by weight over 24 hours. For devices which exhibit water uptake of greater than 1% by weight over 24 hours, typically continuous exposure results in material changes such as brittleness and eventual mechanical failure in standard testing.

The minimal level of iodine concentration needed to achieve sufficient radiopacity to provide clinically acceptable imaging may be determined empirically. In an embodiment, evaluation of identically sized devices formulated from polymers using different weight percentages of iodinated monomer can be compared under simulated clinical use conditions. Using physicians' subjective review and correlating their opinion with the results from an image analysis program, such as Image J, to quantify signal levels, clinically imaging quality is correlated with iodine concentration. The result is a determination of the minimum iodine concentration to assure acceptable image quality. In an embodiment, the minimum iodine concentration value was established at 511 mg/cm$^3$. In an embodiment, the minimum iodine concentration value is above 200 mg/cm$^3$. In an embodiment, the iodine concentration value is between 50 and 600 mg/cm$^3$. As is recognized in the art, the radiopaque atom incorporation range for suitable visualization is dependent on the configuration of the device. In an embodiment, the first repeating unit contains the radiopaque atom(s) and is present in an amount of above 15 wt % of the network. In an embodiment, the first repeating unit contains the radiopaque atom(s) and is present in an amount of above 20 wt % of the network. In an embodiment, the first repeating unit contains the radiopaque atom(s) and is present in an amount of above 30 wt % of the network. In an embodiment, any incorporation of radiopaque moieties that produces a functional product can be used. As described elsewhere, the radiopaque atom(s) can include atoms other than iodine, including bromine or bismuth.

In another embodiment, the signal obtained from a radiopaque polymer device may be compared with that of a platinum device of similar dimensions. In an embodiment where signal level is obtained by x-ray under a 6 inch water phantom, the signal from the radiopaque polymer device may be 70%-90% or 80%-90% of that of the platinum device.

Any polymer that can recover an original shape from a temporary shape by application of a stimulus such as temperature is considered a shape memory polymer (SMP). The original shape is set by processing and the temporary shape is set by thermo-mechanical deformation. A SMP has the ability to recover large deformation upon heating. Shape memory functionality can be utilized to develop medical devices that can be introduced into the body in a less invasive form, wherein the pre-deployed, or temporary, shape is intentionally smaller, or thinner, resulting in a lower profile and a smaller opening (smaller catheter or incision) to introduce the device into the patient than would otherwise be required without the shape change functionality. Then, when stimulated by temperature, typically body temperature but can also be greater than body temperature, the device undergoes shape recovery to return to its permanent, larger form.

A polymer is a SMP if the original shape of the polymer is recovered by heating it above a shape recovery temperature, or deformation temperature ($T_d$), even if the original molded shape of the polymer is destroyed mechanically at a lower temperature than $T_d$, or if the memorized shape is recoverable by application of another stimulus. Any polymer that can recover an original shape from a temporary shape by application of a stimulus such as temperature may be considered a SMP.

From a biomedical device perspective, there are characteristics that are considered favorable in device design. They are quantified in terms of stimuli (such as temperature) driven response, well-defined response temperature, modulus, and elongation. In an embodiment, the thermomechanical properties of the shape memory polymer used to form the device are optimized for one or more of the following: Rubbery modulus ($E_{rub}$), Glass transition temperature ($T_g$), and Speed of recovery (S).

The preferred ranges of rubbery modulus can be different for different applications. The range of moduli of biological tissue can vary from 20 GPa (bone) to 1 kPa (eye) In an embodiment, the rubbery modulus is between 0.1 MPa and 15 MPa at 37° C. In an embodiment, the rubbery modulus is between 0.1 MPa and 50 MPa for the flexible state and between 0.1 to 500 MPa for the rigid state at 37° C. Any rubbery modulus value that produces a functional product can be used. By polymer formulation adjustments, the SMP's modulus, e.g. stiffness, can be established as very soft, on the order of 0.1 MPa. In one embodiment, for use as a device such as an embolic coil, this soft material enhances compaction of the coil pack, shortening the resulting pack for easier placement and ultimately increasing the speed of occlusion. Through other formulations, a higher value can be achieved for the SMP's modulus, such as 15 MPa, to enhance stiffness. In another embodiment, stiffer SMPs can be used to form a tube stent wherein localized stiffness is used to generate outward radial force against a vessel wall when deployed which is required for retention.

In an embodiment, the polymers are selected based on the desired glass transition temperature(s) (if at least one segment is amorphous) taking into consideration the environment of use. In one method, the polymer transition temperature is tailored to allow recovery at the body temperature, $T_r \sim T_g \sim 37°$ C. (A. Lendlein and R. Langer, "Biodegradable, elastic shape-memory polymers for potential biomedical applications." Science, vol. 296, pp. 1673-1676, 2002). The distinct advantage of this approach is the utilization of the body's thermal energy to naturally activate the material. The disadvantage of this approach, for some applications, is that the mechanical properties (e.g., stiffness) of the material are strongly dependent on $T_g$, and can be difficult to alter in the device design process. In particular, it would be difficult to design an extremely stiff device when the polymer $T_g$ is close to the body temperature due to the compliant nature of the polymer. Another possible disadvantage is that the required storage temperature, $T_s$, of a shape memory polymer with $T_g \sim 37°$ C. will typically be below room temperature requiring "cold" storage prior to deployment. In different embodiments, the glass transition temperature of the SMP of the present invention as determined from the peak of tan δ is from 10° C. to 75° C., 20° C. to 50° C., from 25° C. to 50° C., or from 30° C. to 45° C. In different embodiments, the glass transition temperature may be below body temperature (e.g. 25-35° C.), near body temperature (32-42° C.) or above body temperature (40-50° C.). Any $T_g$ value that produces a functional product can be used.

The storage modulus of at least partially non-crystalline polymers decreases in the glass transition region. DMA results highlight the changes that occur as the material is heated from its storage temperature ($T_s$) to its response temperature ($T_r$) and above. FIG. 1 illustrate curves for storage modulus (E') and Tan Delta (ratio of the material's Loss Modulus (E") to Storage Modulus (E')) obtained from dynamic mechanical analysis (DMA) curve of an SMP formulation. This curve illustrates the recovery temperature ($T_r$), the glass transition temperature ($T_g$), the operating temperature ($T_o$) and Tan Delta Peak. Several methods may be used for determining the glass transition temperature; these include the peak or onset of the tan delta curve and the onset of the drop in the storage modulus. The width of the tan Δ peak is an indication of the breadth of the glass transition region. In an embodiment, the glass transition temperature is in the specified ranges and the full width of the tan Δ peak at half maximum is from 10-30° C. or from 10-20° C. The glass transition temperature determined by DMA is frequency dependent and generally increases with increasing frequency. In an embodiment, the measurement frequency is 1 Hz. The glass transition temperature may also depend upon the heating rate and the applied stresses or strains. Other methods of measuring the glass transition temperature include thermal mechanical analysis (TMA) and differential scanning calorimetry (DSC); TMA and DSC are heating rate dependent.

Typically, for each medical device application that incorporates shape recovery, the clinician is anticipating relatively rapid and repeatable shape recovery. In an embodiment, the shape memory polymer devices of the invention produce shape recovery that is fast enough to be detected, completes in a reasonable (intraoperative) time, and repeatable from one device to another. In an embodiment, the shape recovery time can be measured in use or from a screening procedure. The shape recovery time can be measured either from release to 100% recovery or from release to a predetermined amount of recovery.

Figure 2:
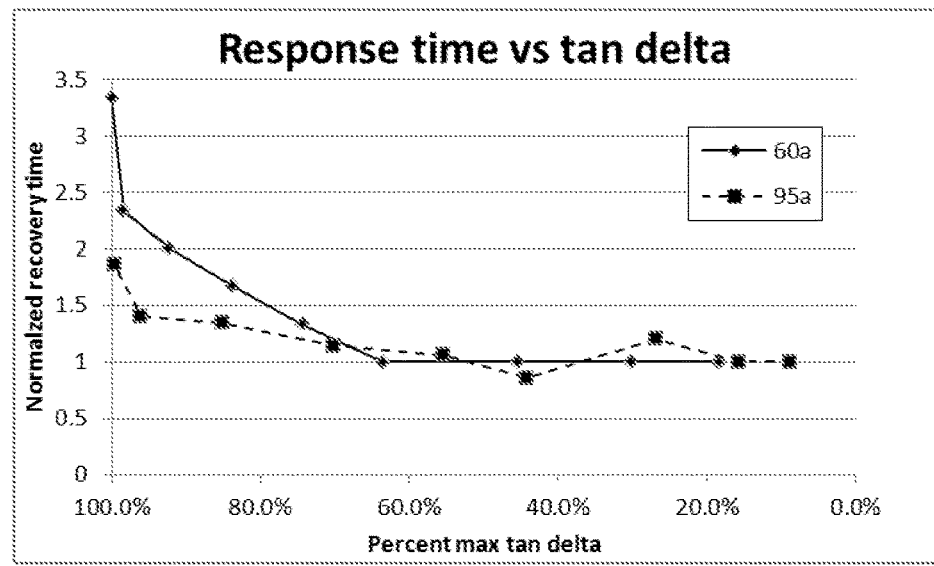
FIG. 2: Recovery time vs. percent max tan delta (with a corresponding material temperature) indicates an asymptotic relationship at which further increasing temperature above $T_g$ has no further effect on increasing the rate of shape change.

The rate of shape change correlates with the rate of storage modulus change on the DMA curve between the operating temperature and $T_r$. For SMPs, rate of shape change can be primarily affected by the temperature difference between $T_o$, the operating temperature (external heating or body core temperature if self actuated), and the polymer's $T_g$ (derived from the formulation). $T_o$ is typically set above $T_r$. Typically, a larger difference between these temperatures will produce a faster rate of change up to an inherent rate limit, or asymptote of the change rate, of the material and device. This limit can be identified by monitoring shape change response time at different temperatures and plotting this relationship. Typically, the amount of response time decreases until it reaches an asymptote. The corresponding $T_o$ reflects the lowest, optimum temperature for the fastest rate of shape change for that material. Increasing the temperature above this point does not induce further reductions in the shape change recover time, e.g. does not further increase the rate of shape change (refer to FIG. 2). In an embodiment this inherent limit, or asymptote begins when $T_o$ is set at the temperature at which the Tan Delta curve is about 60% of its maximum value (refer to FIGS. 1 and 2, when $T_o$ is set above the material's $T_g$). In an embodiment, the polymer's maximum rate of shape change occurs at an environmental operating temperature ($T_o$) that is coincident with the temperature above Tg at which the material's Tan Delta value is equal to 60% of its peak value. The device may be designed so that this optimum temperature is at a useful operating temperature for the device (e.g. at body temperature or another preselected temperature).

In an embodiment, the device is operated at a temperature which is the lowest temperature at which no further increase in shape change rate is seen. In another embodiment, the device is operated at a temperature which is within +/−5° C. of this optimum temperature.

In different embodiments, the recovery ratio of the SMPs employed in the biomedical devices of the invention is greater than 75%, 80%, 90%, 95%, from 80-100%, from 90-100%, or from 95-100%. In various embodiments, the maximum achievable strain is of the radiopaque SMP from 10% to 800%, from 10% to 200%, from 10% to 500%, from 10% to 100%, from 20% to 800%, from 20% to 500%, from 20% to 800%. as measured at a temperature above the glass transition temperature. In different embodiments, the maximum achievable strain or strain to failure of the radiopaque SMP is at least 30% at least 40%, at least 50%, at least 60%, or at least 70%, from 40% to 100%, from 40% to 60%, from 50% to 100%, from 60% to 100% as measured below the glass transition temperature. In different embodiments, the maximum achievable strain or strain to failure of the SMP is at least 30% at least 40%, at least 50%, at least 60%, or at least 70%, from 40% to 100%, from 40% to 60%, from 50% to 100%, from 60% to 100% as measured at ambient temperature (20-25° C.).

In general, the ability of the device (whether technically shape memory or not) to change conformation or configuration (e.g. to expand) is made possible by manufacturing a device having a first conformation or configuration (initial configuration) and, thereafter configuring the device into a second conformation or configuration (temporary or storage configuration), wherein this configuration is at least partially reversible upon the occurrence of a triggering event. After the triggering event, the device assumes a third configuration. In an embodiment, the third configuration (deployed configuration) is substantially similar to the first configuration. However, for an implanted medical device, the device may be constrained from assuming its initial shape (first configuration). In an embodiment, the device is capable of self-expansion to the desired dimensions under physiological conditions.

The invention can provide a variety of radiopaque polymer devices for medical applications, these devices incorporating the polymer compositions of the invention. The devices of the invention can be non-metallic. In different embodiments, these devices can be for purposes of an indwelling, permanent implant to provide the function of: opening, or maintaining an open anatomical lumen; closing an anatomical lumen, either partially as a valve, or complete lumen occlusion for any physiological fluid or gas flow or for a applied therapeutic fluid or gas flow; support of an anatomical structure to assist in therapeutic restoration of an organ, vascular, digestive, excrement, or airway function; support of an anatomical structure to assist in therapeutic restoration of an orthopaedic, maxillofacial, spinal, joint or other skeletal or function; to support hemostasis by covering an area inside the body after tissue dissection or resection, a patch, such as for hemostasis of the liver, or other organ, In other embodiments, these devices can be used for purposes of a diagnostic or therapeutic instrument or device to provide the function of: a catheter for the purposes of accessing an anatomical location; delivering another device and/or therapeutic agent; or controlling the access or delivery of another device and/or therapeutic agent; a temporarily indwelling device to provide a limited time therapeutic benefit, such as a vena cava filter that is placed in a vessel, left indwelling for a period of time, for example to capture blood clots, and subsequently removed when the therapeutic period is completed.

In one embodiment for neurovascular cases, wherein intracranial aneurysms are repaired, current state of care may use very fine metal (platinum) based embolic coils delivered into the aneurysm sack to fill this space and effect an isolation of the weakened vessel wall from the parent vessel thereby reducing the risk of rupture and stroke. However, because of the metallic nature of these devices, two deficiencies typically occur: 1. Approximately 25% of these patients must return for retreatment as the aneurysm continues to grow, and 2. To diagnose the need for retreatment, many of these patients must have an invasive angiogram (contrast injection) of the aneurysm area under fluoroscopy to be able to visualize the condition given that the metal coil materials are not compatible with MRI or CT Scan imaging modalities. A non-metallic, radiopaque SMP embolic device for aneurysm repair does not suffer this limitation in imaging capability Although the description herein contains many specificities, these should not be construed as limiting the scope of the invention but as merely providing illustrations of some of the presently preferred embodiments of the invention. For example, thus the scope of the invention should be determined by the appended claims and their equivalents, rather than by the examples given.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a compound or composition is claimed, it should be understood that compounds or compositions known in the art including the compounds or compositions disclosed in the references disclosed herein are not intended to be included. When a Markush group or other grouping is used herein, all individual members of the group and all combinations and subcombinations possible of the group are intended to be individually included in the disclosure.

In the moieties and groups described herein, it is understood that the valence form of the group that is required to fulfill its purpose in the description or structure is included, even if not specifically listed. For example, a group that is technically a "closed shell" group as listed or described can be used as a substituent in a structure, as used herein. For every closed shell moiety or group, it is understood that a group corresponding to a non-closed structural moiety is included, for use in a structure or formula disclosed herein.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, device elements, starting materials, and synthetic methods, and other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, a composition range or a mechanical property range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art. The preceding definitions are provided to clarify their specific use in the context of the invention.

The invention may be further understood by the following non-limiting examples.

Example 1: Water Uptake of Radiopaque SMPs with Hydrophilic and Hydrophobic Crosslinkers All polymers tested included the iodinated monomer of Formula 15 (TIA). Compositions with hydrophilic poly(ethylene glycol) dimethacrylate (PEGDMA) (MW 550 and 1000) or poly(ethylene glycol) diacrylate (PEGDA) (MW 575 and 700) crosslinkers were demonstrated to result in water absorption in test samples of more than 1% by weight in a 24 hour period. Subsequent continuous exposure resulted in material changes such as brittleness and eventual mechanical failure in standard testing. Conversely, in a different embodiment, use of hydrophobic crosslinker or crosslinkers, such as poly(tetrahydrofuran) (PTHF) or the monomer of formula 9 with $R^9$ being C10 (C10-DA), was demonstrated to result in very low water absorption, below 1% by weight in a 24 hour period. Similarly, these materials incorporating hydrophobic crosslinkers have shown negligible deterioration with continued exposure to an aqueous environment.

Example 2: DSC Measurements on a Radiopaque SMP

Figure 3:
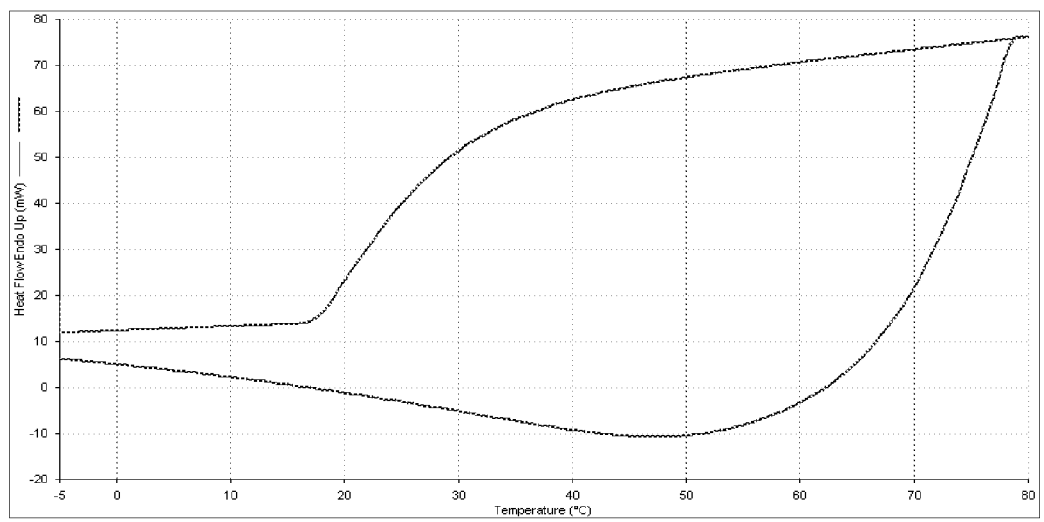
FIG. 3: Differential scanning calorimetry DSC curve for an SMP formulation showing no crystallinity features in the scan.

FIG. 3 illustrates a DSC curve for a radiopaque SMP formulation employing "TIA" monomer (Formula 15) and decanedioldiacryalate (DDA) crosslinker. FIG. 3 indicates that no crystalline features were observed in the scan.

Example 3: Exemplary Radiopaque Polymer Devices

Shape memory polymer devices and other non-shape memory polymer devices of the invention can incorporate material formulations that utilize a suitable glass transition temperature within a range about body core temperature. To achieve different performance requirements, the polymer's $T_g$ may be intentionally suppressed below body temperature resulting in shape change occurrence immediately upon release from any physical constriction.

Figure 4:
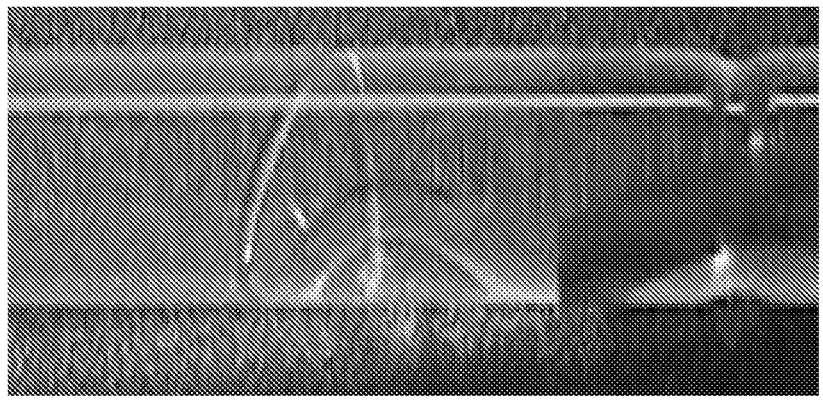
FIGS. 4a-b: Embolic coils exiting from very thin, single lumen catheters to form an occlusive mass much larger than the diameter of the coil.
Figure 4:
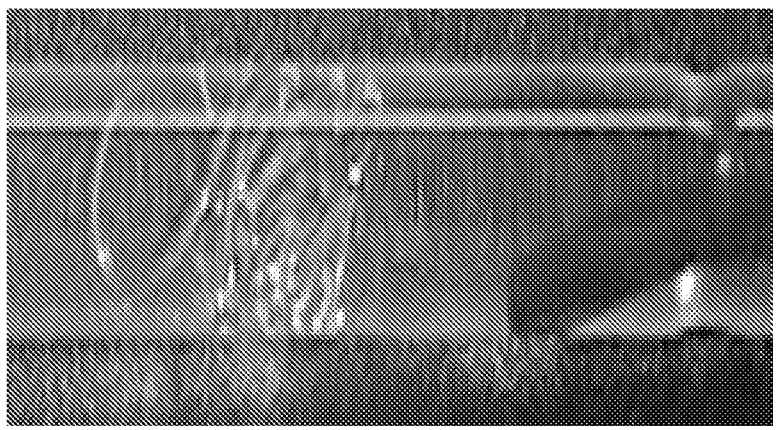

In one embodiment, an SMP with a $T_g$ of 25° C. has been utilized to accelerate the rate of shape change of an embolic coil upon expulsion from a small lumen catheter. One form of embolic devices forms a large curl of 10 mm in diameter but is constructed of an SMP wire that is only 0.032" in diameter. The wire can be formed into a pre-deployed curled shape that is straightened to allow delivery of these devices in a small diameter catheter (<5 fr). When deployed into the blood stream, these devices recovered their curl shape to effectively occlude a 9 mm vessel, with the 1 mm oversize assuring sufficient radial force from the material modulus and deflection to provide effective anchoring so that the embolic device doesn't migrate under the influence of blood flow in the vessel. FIGS. 4a-b show images embolic coils exit from very thin, single lumen catheters to form an occlusive mass much larger than the diameter of the coil. FIG. 4a shows the coil after initial entry. FIG. 4b shows the coil after deployment.

Likewise, the polymer's $T_g$ may be set above body temperature wherein an external heating device is used to provide the physician with a discretionary shape change function. In another embodiment, an SMP with a $T_g$ of 50° C. has been used to place and accurately position a tube stent within an anatomical lumen. Maintaining its low profile, predeployed temporary shape benefits the physician's ability to move and accurately locate the device prior to deployment. When held in the desired position, the device is heated to its $T_r$ by flushing with warmed saline irrigation which causes shape recovery to occur to the stent's permanent shape.

Yet, another embodiment is the use of an SMP with an elevated $T_g$ of 42° C. (just above body core temperature) that is used as a clasp for retaining a deployed device. In its permanent shape, the clasp is open, in its temporary shape, the clasp is closed. The clasp connects a device, such as a vena cava filter, the filter itself may be made from a different SMP, to a delivery guidewire that contains electrical conductors joined to a heating element adjacent to the clasp. With the SMP clasp closed in its temporary shape (below $T_g$), the device is advanced into the bloodstream. Upon reaching its desired position, the clasp is heated through an external low voltage passing down the conductors and through the heating element. Upon the temperature reaching $T_r$, the clasp opens to its recovered, permanent shape, releasing the vena cava filter.

In yet another embodiment, an SMP with an elevated $T_g$ of 42° C. (just above body core temperature) is used within a section of a mono-directional catheter. The catheter section is formed with a permanent curved shape to allow specific direction of the tip of the catheter. As a straight catheter is easier to manipulate into position, the temporary shape is straight but not necessarily stiff. Upon entry into the body, below $T_g$, the straight catheter is easily manipulated to a target location wherein it is warmed by an externally heated, internal delivery wire, or by warmed saline solution flushed through the catheter. Upon the material temperature reaching $T_r$, the catheter section curls, returning to its recovered, permanent shape, providing specific direction for the catheter tip during use. Meanwhile, the curvature is not so stiff as to preclude simply retrieving the catheter after use.

Example 4: Synthesis of TIA

A round-bottom flask was charged with 2,3,5-triiodobenzoic acid (100.097 g; 200.6 mmoles) and 325 g thionyl chloride. The system was refluxed, and then the excess thionyl chloride was removed with a rotary evaporator—at a temperature of 60° C. until solvent was no longer visible. The solid was then redissolved with 250 mL of anhydrous toluene. In a separate round-bottom flask, 2-hydroxyethyl-acrylate (35.84 g; 308.6 mmoles) was dissolved in 100 mL toluene, and the system was dried using a small quantity of anhydrous magnesium sulfate, and pyridine (19 g; 240 mmoles). The solution of 2-hydroxyethyl-acrylate and pyridine in toluene was added to the acid chloride solution, followed by mixing. The supernatant solution was decanted, extracted with 1N HCl, 1N sodium bicarbonate and water, then dried with anhydrous magnesium sulfate and filtered. The solution volume was reduced to half by rotary evaporation, and then the solution was allowed to precipitate which was purified by dissolving in hexane, and filtered at chilled temperature. The recrystallized solid was filtered and dried.

Example 5: Synthesis of Dimer Diol Diacrylate (DIDA)

Charge Dimer diol (26.85 g) and toluene (300 mL) to a 3-neck flask. The flask was stirred under heat to initiate azeotropic distillation under a nitrogen atmosphere until about 100 mL of distillate was collected was and cooled to 60° C. The 3-neck flask was charged with triethylamine (14.6 mL) and followed by acryloyl chloride (8.1 mL). The system was stirred for 60 minutes. The system was extracted with 150 mL of 1N HCl, 150 mL of 1N sodium bicarbonate, and 150 mL of distilled water. The organic layer was dried with anhydrous magnesium sulfate and filtered. 0.3 g of 1% hydroquinone in acetone was added, then all solvent removed with a rotary evaporator and then by stirring the viscous solution while sparing with nitrogen.

Example 6: Synthesis of Poly(THF) Diacrylate MW 360

Charge Poly(THF), MW 250 diol (10.0 g) and bulk toluene (300 mL) to 3-neck flask. Heat and stir to initiate azeotropic distillation under a nitrogen atmosphere until about 100 mL of distillate is collected and cool to 60° C. Charge to the 3-neck flask triethylamine (12.2 mL) and then drip in acryloyl chloride (6.8 mL). React for 60 minutes. Extract system with 100 mL of 1N HCl, 100 mL of 1N sodium bicarbonate, and 100 mL of distilled water. Dry organic layer with anhydrous magnesium sulfate and filter. Add 0.15 g of 1% hydroquinone in acetone, then remove solvent first with a rotary evaporator and then by stirring the viscous solution while sparging with nitrogen.

Example 7: Synthesis of Poly(Hexamethylene Carbonate) Diacrylate (MW 975)

Charge poly(hexamethylene carbonate) (PHMC) MW 865 (12.45 g) and anhydrous toluene (300 mL) to 3-neck flask. Start stirring and heat to initiate azeotropic distillation under a nitrogen atmosphere until about 100 mL of distillate was collected and cooled to 60° C. Charge triethylamine (3.52 g) to flask and add acryloyl chloride (2.6 mL). React for 60 minutes. Extract system with 100 mL of 1N HCl, 100 mL of 1N sodium bicarbonate, and 100 mL of distilled water. Dry organic layer with anhydrous magnesium sulfate and filter into a round-bottom flask. Add 0.15 g of 1% hydroquinone in acetone, then remove solvent first with a rotary evaporator and then by stirring the viscous solution while sparging with nitrogen.

Example 8: Formulation of SMP with TIA and Decanediol Diacrylate (DDA), Part Fabrication A. A 20 mL scintillation vial was charged with: Irgacure 819 (0.0038 g), n-butyl acrylate (0.38 g) and decanediol diacrylate (0.20 g) and heated to dissolve the photoinitiator. Add TIA (0.42 g) and heat followed by swirling of the vial to homogenize all components.

B. The system was transferred to a mold in a heated chamber and quickly transferred to the light source to prevent pre-cure solidification of the formulation. Photocuring at 1 mW/cm$^2$ for at least 20 minutes was followed by at least 60 minutes of post-cure heating above 100° C.

Example 9: Formulation of SMP with TIA and Poly(THF) Diacrylate MW 360, Part Fabrication A. A 20 mL scintillation vial was charged with: Irgacure 819 (0.0302 g), n-butyl acrylate (1.490 g) and poly(THF) diacrylate; MW 360 (0.760 g) and heated to dissolve the photoinitiator. Add TIA (3.726 g) and heat, followed by swirling of the vial to homogenize all components.

B. The system was transferred to a mold in a heated chamber and quickly transferred to the light source to prevent pre-cure solidification of the formulation. Photocuring at 1 mW/cm$^2$ for at least 20 minutes was followed by at least 60 minutes of post-cure heating at above 100° C.

Example 10: Formulation of SMP with TIA and Bisphenol A Propoxylate Diacrylate, Part Fabrication A. A 20 mL scintillation vial was charged with: Irgacure 819 (0.0050 g), n-butyl acrylate (0.400 g) and Bisphenol A diacrylate (0.110 g) and heated to dissolve the photoinitiator. Add TIA (0.500 g) and heat followed by swirling of the vial to homogenize all components.

B. The system was transferred to a mold in a heated chamber and quickly transferred to light source to prevent pre-cure solidification of the formulation. Photocuring at 1 mW/cm$^2$ for at least 20 minutes was followed by at least 60 minutes of post-cure heating at above 100° C.

Example 11: Formulation of SMP with TIA, DDA and PDMS Dimethacrylate MW 465, Part Fabrication A. A 20 mL scintillation vial was charged with: Irgacure 819 (0.0080 g), n-butyl acrylate (0.567 g) and DDA (0.502 g) and polydimethylsiloxane dimethacrylate MW 465 (0.110 g) and heat to dissolve the photoinitiator. Add TIA (0.813 g) and heat followed by swirling of the vial to homogenize all components.

B. The system was transferred to a mold in a heated chamber and quickly transferred to the light source to prevent pre-cure solidification of the formulation. Photocuring at 1 mW/cm² for at least 20 minutes was followed by at least 60 minutes of post-cure heating at above 100° C.

Example 12: Formulation of SMP with TIA and PHMCDA MW 975, Part Fabrication

A. A 20 mL scintillation vial was charged with: Irgacure 819 (0.0100 g), n-butyl acrylate (0.300 g), and PHMCDA (0.400 g) and heat to dissolve the photoinitiator. Add TIA (1.30 g) and heat followed by swirling of the vial to homogenize all components.

B. The system was transferred to a mold in a heated chamber and quickly transferred to the light source to prevent pre-cure solidification of the formulation. Photocuring at 1 mW/cm² for at least 20 minutes was followed by at least 60 minutes of post-cure heating at above 100° C.

Example 13: Formulation of SMP with TIA and DIDA, Part Fabrication

A. A 20 mL scintillation vial was charged with: Irgacure 819 (0.0055 g), n-butyl acrylate (0.329 g), and DIDA (0.566 g) and heat to dissolve the photoinitiator. Add TIA (1.096 g) and heat followed by swirling of the vial to homogenize all components.

B. The system was transferred to a mold in a heated chamber and quickly transferred to the light source to prevent pre-cure solidification of the formulation. Photocuring at 1 mW/cm² for at least 20 minutes was followed by at least 60 minutes of post-cure heating at above 100° C.

Example 14: Post-Modification of Crosslinked or Pre-Crosslinked Segments Containing Styryl Aromatic Rings As shown below in Scheme 1, prepolymerized segments can be used in the compositions here. In an embodiment, the radiopaque functionality can be incorporated using methods known in the art, including the exemplary synthesis methods shown below.

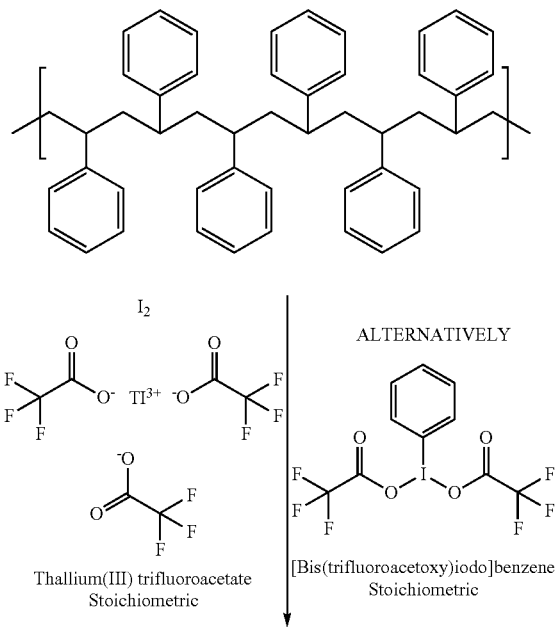

Scheme 1

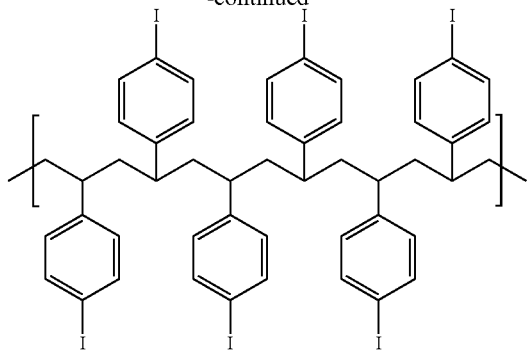

54.7% by weight iodine in polystyrene segment if quantitative iodination is achieved Example 15: Iodination Chemistry for Styryl Units Including Polymerized Styryl Units of SEPS, SIBS or Other Polystyrene Hard-Block-Containing TPEs The following is an exemplary synthesis method. Alternatives and modifications are known in the art.

Dissolve Kuraray SEPS S2004 (thermoplastic elastomer comprised of 18% polystyrene, 72% fully hydrogenated ethylene-propylene copolymer; 20.0 g) in 500 mL dichloromethane in a 3-neck, 1 L flask. When SEPS polymer is fully dissolved, add [bis(trifluoroacetoxy)iodo]benzene (14.9 g) to the flask and stir at ambient temperature for 16 hours. Transfer the dichloromethane reaction solution to a separatory funnel. Charge 1.5 L isopropanol to a large jar, stir rapidly with a magnetic stirrer, and drip the dichloromethane reaction solution into the isopropanol to precipitate the polymer. Filter the solid on a coarse frit funnel, transfer the solid to a large beaker, cover the beaker with aluminum foil with small perforations in the foil, and vacuum dry at 60° C. for 6 hours. Redissolve the dried polymer in 500 mL dichloromethane, reprecipitate in 1.5 L isopropanol, and vacuum dry the filtered solid at 60° C. for 6 hours twice. Yield: 15.7 g of a pale-yellow, spongy material anticipated to be fully 4-iodinated in the polystyrene block segments, thus converting the polymer composition to 67% SEPS, 33% PS-I, a target PS-based hardblock content for optimal elastomeric properties, with the Tg of the hard block raised from 100° C. (PS) to 156° C. (PS-I), the latter but not the former temperature expected to be amenable to typical autoclave sterilization conditions of 121-134° C. (Reference: Yudina et al., "Aspects of Direct Iodination of Polystyrene in Presence of [bis(Trifluoroacetoxy)Iodo]Benzene, *Polymer Science USSR*, 31(6), 1318-1823 (1989).

I claim:

1. A polymer composition comprising a crosslinked network, the network comprising:
   a) a first repeating unit represented by one of Formula 1, 1-A, 1-B or 1-C:

(Formula 1)

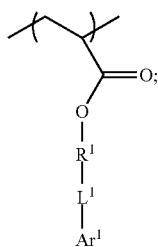

(Formula 1-A)

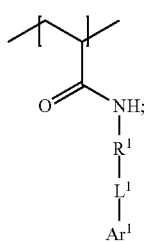

(Formula 1-B)

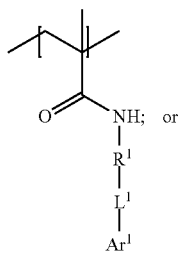

(Formula 1-C)

wherein X is Br or I;

m is an integer from 3 to 5;

$R^1$ is substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, or $C_5$-$C_{36}$ heteroarylene;

$L^1$ is a single bond, —(CH$_2$)$_n$—, —(HCCH)$_n$—, —O—, —S—, —SO—, —SO$_2$—, —SO$_3$—, —OSO$_2$—, —NR$^2$—, —CO—, —COO—, —OCO—, —OCOO—, —CONR$^3$—, —NR$^4$CO—, —OCONR$^5$—, —NR$^6$COO—, or —NR$^7$CONR$^8$—;

$Ar^1$ is a $C_5$-$C_{30}$ aryl or $C_5$-$C_{30}$ heteroaryl that is substituted with three or more I, Br or Bi atoms;

each of $R^2$-$R^8$ is independently hydrogen or $C_1$-$C_{10}$ alkyl; and n is an integer selected from the range of 1 to 16;

wherein the amount of the first repeating unit in the polymer composition is from 15 to 35 wt %; and b) a second repeating unit represented by Formula 2:

(Formula 2)

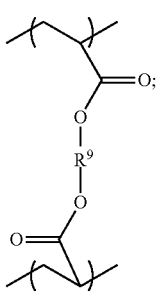

wherein $R^9$ is (Formula 4)

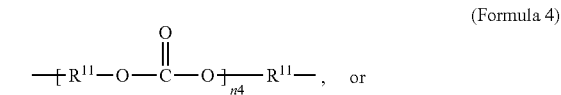

or (Formula 4-A)

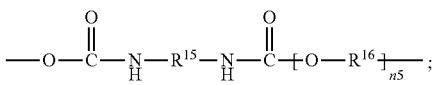

wherein $R^{11}$ is $C_6$-$C_{20}$ alkylene and $n_4$ is an integer from 1 to 50; and wherein the amount of the second repeating unit in the polymer composition is from 65 to 85 wt %.

2. The polymer composition of claim 1, wherein the first repeating unit is represented by Formula 1-D, (Formula 1-D)

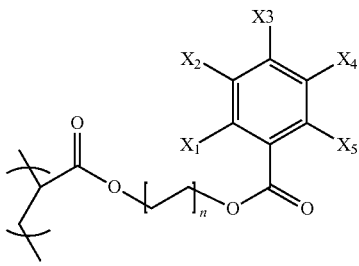

wherein n is an integer from 1 to 8, each of $X_1$-$X_5$ is iodine or hydrogen and at least three of $X_1$-$X_5$ are iodine.

3. The polymer composition of claim 1, wherein the second repeating unit is represented by Formula 2-B, where $R^{11}$ is $C_6$-$C_{20}$ alkylene and $n_4$ is an integer from 1 to 25

(Formula 2-B)

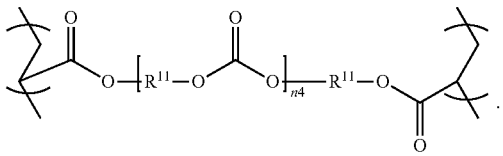

4. The polymer composition of claim 1, wherein the network further comprises an additional repeating unit represented by Formula 7:

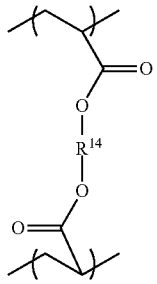

(Formula 7)

where $R^{14}$ is substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, an oligomeric polyester, an oligomeric polycarbonate, an oligomeric polyurethane,

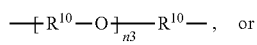 (Formula 3)

or

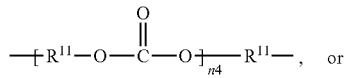 (Formula 4)

or

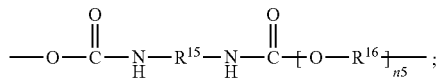 (Formula 4-A)

wherein $R^{10}$ is $C_4$-$C_{20}$ alkylene and $n_3$ is an integer from 1 to 50 or wherein $R^{11}$ is $C_3$-$C_{20}$ alkylene and $n_4$ is an integer from 1 to 50, and $R^{14}$ is other than $R^9$.

5. The polymer composition of claim 4, wherein the combined amount of the second repeating unit and the repeating unit of claim 4 is from 65 to 85 wt % of the polymer composition.

6. A polymer composition comprising a crosslinked network formed by polymerization of a monomer mixture comprising:

a) a first monomer having the general structure of one of Formula 8, 8-A, 8-B or 8-C

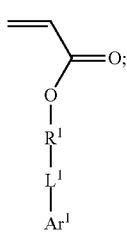 (Formula 8)

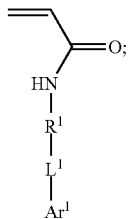 (Formula 8-A)

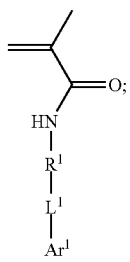 (Formula 8-B)

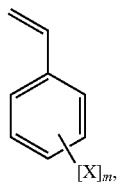 (Formula 8-C)

wherein X is Br or I;
m is an integer from 3 to 5;
wherein $R^1$ is substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, or $C_5$-$C_{36}$ heteroarylene;
$L^1$ is a single bond, —(CH$_2$)$_n$—, —(HCCH)$_n$—, —O—, —S—, —SO—, —SO$_2$—, —SO$_3$—, —OSO$_2$—, —NR$^2$—, —CO—, —COO—, —OCO—, —OCOO—, —CONR$^3$—, —NR$^4$CO—, —OCONR$^5$—, —NR$^6$COO—, or —NR$^7$CONR$^8$—;
$Ar^1$ is a $C_5$-$C_{30}$ aryl or $C_5$-$C_{30}$ heteroaryl that is substituted with three or more I, Br or Bi atoms; and
each of $R^2$-$R^8$ is independently hydrogen or $C_1$-$C_{10}$ alkyl;
n is an integer selected from the range of 1 to 16;
wherein the amount of the first monomer is from 15 to 35 wt % of the monomer mixture; and b) a second monomer having the general structure of Formula 9

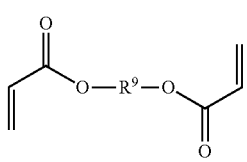 (Formula 9)

wherein $R^9$ is

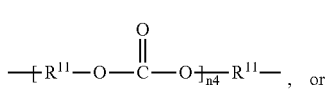 (Formula 4)

or

-continued (Formula 4-A)

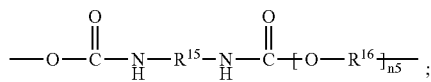

wherein $R^{11}$ is $C_6$-$C_{20}$ alkylene and $n_4$ is an integer from 1 to 50; and wherein the amount of the second monomer is from 65 to 85 wt % of the monomer mixture.

7. The polymer composition of claim 6, wherein the structure of the first monomer is given by Formula 13-A, (Formula 13-A)

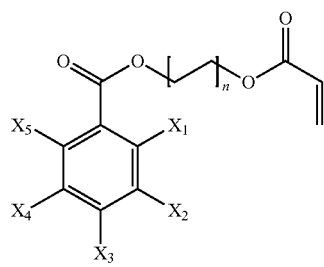

and at least three of $X_1$-$X_5$ are iodine and n is an integer from 1 to 8.

8. The polymer composition of claim 6 wherein the second monomer has the structure of Formula 9-A where $R^{11}$ is $C_6$-$C_{20}$ alkylene and $n_4$ is an integer from 1 to 25

(Formula 9-A)

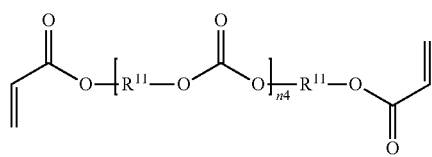

9. The polymer composition of claim 6, wherein the mixture further comprises a monomer having the general structure of Formula 12

(Formula 12)

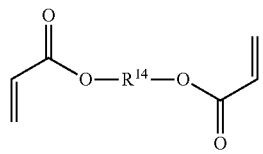

wherein $R^{14}$ is substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, an oligomeric polyester, an oligomeric polycarbonate, an oligomeric polyurethane, (Formula 3)

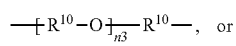, or (Formula 4)

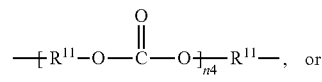, or (Formula 4-A)

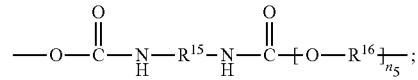;

wherein $R^{10}$ is $C_4$-$C_{20}$ alkylene and $n_3$ is an integer from 1 to 50 or wherein $R^{11}$ is $C_3$-$C_{20}$ alkylene and $n_4$ is an integer from 1 to 50 and $R^{14}$ is other than $R^9$.

10. The polymer composition of claim 9, wherein the amount of the combined amount of the second monomer and the monomer of claim 9 is from 65 to 85 wt % of the monomer mixture.

11. A method for making a polymer composition comprising a crosslinked network, the method comprising the steps of:

a) forming a monomer mixture comprising i) a first monomer having the general structure of one of Formula 8, 8-A, 8-B or 8-C (Formula 8)

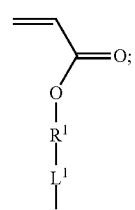

(Formula 8-A)

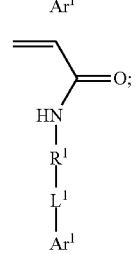

(Formula 8-B)

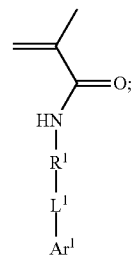

(Formula 8-C)

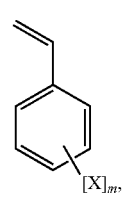

wherein X is Br or I;

m is an integer from 3 to 5;

wherein $R^1$ is substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, or $C_5$-$C_{36}$ heteroarylene;

$L^1$ is a single bond, —$(CH_2)_n$—, —(HCCH)$_n$—, —O—, —S—, —SO—, —SO$_2$—, —SO$_3$—, —OSO$_2$—, —NR$^2$—, —CO—, —COO—, —OCO—, —OCOO—, —CONR$^3$—, —NR$^4$CO—, —OCONR$^5$—, —NR$^6$COO—, or —NR$^7$CONR$^8$—;

$Ar^1$ is a $C_5$-$C_{30}$ aryl or $C_5$-$C_{30}$ heteroaryl that is substituted with three or more I, Br or Bi atoms; and each of $R^2$-$R^8$ is independently hydrogen or $C_1$-$C_{10}$ alkyl;

n is an integer selected from the range of 1 to 16;

wherein the amount of the first monomer is from 15 to 35 wt % of the monomer mixture; and ii) a second monomer having the general structure of Formula 9

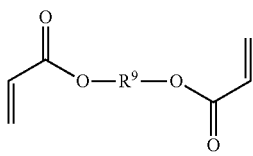

(Formula 9)

wherein $R^9$ is

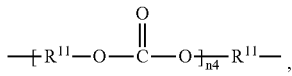

(Formula 4)

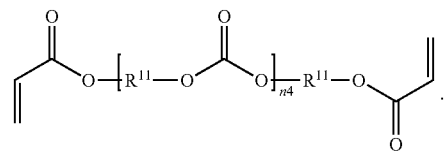

(Formula 4-A)

wherein $R^{11}$ is $C_6$-$C_{20}$ alkylene and $n_4$ is an integer from 1 to 50; and $R^{14}$ is other than $R^9$; and wherein the amount of the second monomer is from 65 to 85 wt % of the total amount of monomer in the monomer mixture; and iii) a free radical initiator; and b) polymerizing the monomer mixture.

12. The method of claim 11, wherein during step b) the monomer mixture is held at a temperature between 65° C. and 150° C.

13. The method of claim 11, wherein the method further comprises a curing step following step b), wherein the curing temperature is from 50° C. and 150° C. and the curing time from 5 seconds to 60 minutes.

14. The method of claim 11, wherein the structure of the first monomer is given by Formula 13-A,

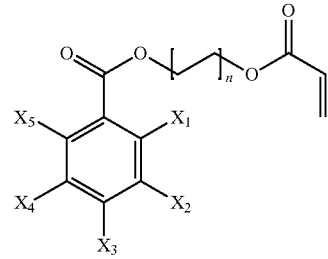

(Formula 13-A)

at least three of $X_1$-$X_5$ are iodine and n is an integer from 1 to 8.

15. The method of claim 11, wherein the second monomer has the structure of Formula 9-A where $R^{11}$ is $C_6$-$C_{20}$ alkylene and $n_4$ is an integer from 1 to 25

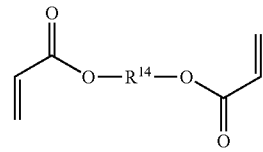

(Formula 9-A)

16. The method of claim 11, wherein the mixture further comprises a monomer having the general structure of Formula 12

(Formula 12)

wherein $R^{14}$ is substituted or unsubstituted $C_2$-$C_{36}$ alkylene, $C_2$-$C_{36}$ cycloalkylene, $C_2$-$C_{36}$ alkenylene, $C_2$-$C_{36}$ cycloalkenylene, $C_2$-$C_{36}$ alkynylene, $C_5$-$C_{36}$ arylene, $C_5$-$C_{36}$ heteroarylene, an oligomeric polyester, an oligomeric polycarbonate, an oligomeric polyurethane,

(Formula 3)

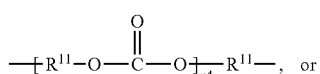

(Formula 4)

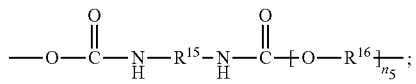

(Formula 4-A)

wherein $R^{10}$ is $C_4$-$C_{20}$ alkylene and $n_3$ is an integer from 1 to 50 or wherein $R^{11}$ is $C_3$-$C_{20}$ alkylene and $n_4$ is an integer from 1 to 50, and $R^{14}$ is other than $R^9$.

17. The method of claim 16, wherein the combined amount of the second monomer and the monomer of claim 16 is from 65 to 85 wt % of the monomer mixture.

18. The polymer composition of claim 2, wherein n is an integer from 3 to 8.

19. The polymer composition of claim 7, wherein n is an integer from 3 to 8.

20. The polymer composition of claim 4, wherein n is an integer from 3 to 8.

* * * * *